(12) United States Patent
Ohmura

(10) Patent No.: US 11,291,367 B2
(45) Date of Patent: Apr. 5, 2022

(54) OPHTHALMIC IMAGING OPTICAL SYSTEM, OPHTHALMIC IMAGING APPARATUS, OPTOMETRIC IMAGE ACQUISITION METHOD, AND OPTOMETRIC IMAGING SYSTEM

(71) Applicant: NIKON CORPORATION, Tokyo (JP)

(72) Inventor: Yasuhiro Ohmura, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 245 days.

(21) Appl. No.: 16/664,102

(22) Filed: Oct. 25, 2019

(65) Prior Publication Data

US 2020/0054212 A1 Feb. 20, 2020

Related U.S. Application Data

(63) Continuation of application No. PCT/JP2018/015613, filed on Apr. 13, 2018.

(30) Foreign Application Priority Data

Apr. 28, 2017 (JP) .............................. JP2017-089976

(51) Int. Cl.
*A61B 3/14* (2006.01)
*A61B 3/107* (2006.01)
*A61B 3/12* (2006.01)
*A61B 3/00* (2006.01)
*A61B 3/10* (2006.01)

(52) U.S. Cl.
CPC ................ *A61B 3/14* (2013.01); *A61B 3/107* (2013.01); *A61B 3/12* (2013.01); *A61B 3/0041* (2013.01); *A61B 3/102* (2013.01)

(58) Field of Classification Search
CPC .. A61B 3/14; A61B 3/107; A61B 3/12; A61B 3/0041; A61B 3/102; A61B 3/10; A61B 3/13
See application file for complete search history.

(56) References Cited

U.S. PATENT DOCUMENTS

| 4,003,642 A | 1/1977 | Vogeley |
| 5,004,331 A | 4/1991 | Haseltine |
| (Continued) | | |

FOREIGN PATENT DOCUMENTS

| JP | 2000-504251 A | 4/2000 |
| JP | 2000-206410 A | 7/2000 |
| (Continued) | | |

*Primary Examiner* — Mohammed A Hasan
(74) *Attorney, Agent, or Firm* — Foley & Lardner LLP

(57) ABSTRACT

Both observation of a wide range within a subject eye may be enabled and a burden on a subject of whom the subject eye is part may be moderated. In order of incidence of light from a side at which a pupil of the subject eye is disposed, spreading of the luminous flux is suppressed by a first refracting face, the light is reflected by a first reflection surface with a central aperture, directing the luminous flux in convergent directions in a direction toward the subject eye, the light is reflected in the direction opposite to the direction toward the subject eye by a second reflection surface, and the light is transmitted through the central aperture of the first reflection surface and forms a pupil conjugate image that is conjugate with a position of the pupil of the subject eye.

16 Claims, 23 Drawing Sheets

(56) References Cited

U.S. PATENT DOCUMENTS

| | | | |
|---|---|---|---|
| 6,164,779 A | * | 12/2000 | Volk ................. A61B 3/125 |
| | | | 351/219 |
| 6,473,243 B1 | | 10/2002 | Omura |
| 6,621,557 B2 | | 9/2003 | Takahashi |
| 2011/0143287 A1 | | 6/2011 | Ohmura |
| 2013/0093996 A1 | | 4/2013 | Thomson |

FOREIGN PATENT DOCUMENTS

| | | | | |
|---|---|---|---|---|
| JP | 3346775 B2 | | | 11/2002 |
| JP | 2013-524978 A | | | 6/2013 |
| JP | 2016140360 A | * | | 8/2016 |
| WO | WO-1998/017170 A1 | | | 4/1998 |
| WO | WO-2012/095620 A1 | | | 7/2012 |

* cited by examiner

OPHTHALMIC IMAGING OPTICAL SYSTEM, OPHTHALMIC IMAGING APPARATUS, OPTOMETRIC IMAGE ACQUISITION METHOD, AND OPTOMETRIC IMAGING SYSTEM

CROSS-REFERENCE TO RELATED APPLICATION

This application is a continuation application of International Application No. PCT/JP2018/015613, filed Apr. 13, 2018, the disclosure of which is incorporated herein by reference in its entirety. Further, this application claims priority from Japanese Patent Application No. 2017-089976, filed Apr. 28, 2017, the disclosure of which is incorporated herein by reference in its entirety.

TECHNICAL FIELD

The disclosed technology relates to an ophthalmic imaging optical system, an ophthalmic imaging apparatus, an optometric image acquisition method, and an optometric imaging system.

BACKGROUND ART

In ophthalmology, a number of ophthalmic imaging apparatuses have been realized that enable observation of the interior of the eye of a subject (below referred to as "the subject eye"), particularly the fundus region of the subject eye, for purposes of eye examinations and surgical treatment of eyes. For example, a technology is known (see Patent Document 1) that relates to an observation apparatus that creates a real image of the fundus of the subject eye. In the present Description, the meaning of the term "ophthalmic" is intended to include fields of medicine relating to the eyes.

In the technology recited in Patent Document 1, a lens element featuring a concave surface with a shape that matches the curvature of the cornea is put into close contact with the subject eye (the cornea), and an optical system including this close-contact lens element is configured to form a real image of the fundus region of the subject eye.

RELATED ART REFERENCES

Patent Documents

Patent Document 1: Japanese Patent Application National Publication No. 2000-504251

SUMMARY OF INVENTION

Technical Problem

The disclosed technology provides an ophthalmic imaging optical system, an ophthalmic imaging apparatus, an optometric image acquisition method, and an optometric imaging system that, compared to a situation in which a lens element is put into close contact with a subject eye and the interior of the subject eye is observed, both may moderate a burden on a subject of whom the subject eye is part and may enable observation of a wide range within the subject eye.

Solution to Problem

An ophthalmic imaging optical system according to a first aspect of the disclosed technology includes a first optical unit and a second optical unit that are disposed on the same optical axis in this order from a side thereof at which a subject eye is disposed. The first optical unit includes: a first reflection surface that includes an aperture portion centered on the optical axis; and a second reflection surface that reflects light reflected from the first reflection surface toward an opposite side of the subject eye, and the first optical unit and the second optical unit form a conjugate position that is conjugate with a pupil position of the subject eye, at an opposite side of the subject eye.

In an ophthalmic imaging optical system according to a second aspect, in the ophthalmic imaging optical system according to the first aspect, the first reflection surface and the second reflection surface are formed with rotational symmetry about the optical axis.

In an ophthalmic imaging optical system according to a third aspect, in the ophthalmic imaging optical system according to the second aspect, the first optical unit is disposed such that light from the pupil of the subject eye is transmitted through a refracting surface which is concave relative to the subject eye and is disposed closest to the subject eye, and reflected by the first reflection surface and the second reflection surface, and passed through the aperture portion of the first reflection surface.

In an ophthalmic imaging optical system according to a fourth aspect, in the ophthalmic imaging optical system according to the third aspect, the first reflection surface is a reflective surface that is formed in a concave shape, the second reflection surface is a reflective surface that is formed in a convex shape and includes an aperture centered on the optical axis, and the first and second reflection surfaces form an annular image of a portion of the subject eye.

In an ophthalmic imaging optical system according to a fifth aspect, in the ophthalmic imaging optical system according to the fourth aspect, the first reflection surface is a reflective surface formed at a surface of a material with a refractive index greater than 1, and reflects light that is incident through the material with the refractive index greater than 1, and the second reflection surface includes an aperture portion that transmits light at a central portion thereof containing the optical axis.

In an ophthalmic imaging optical system according to a sixth aspect, in the ophthalmic imaging optical system according to the fourth aspect, the first reflection surface and the second reflection surface are formed at each of two opposing sides of a material with a refractive index greater than 1, and are reflecting surfaces that reflect light that is incident through the material with the refractive index greater than 1, the second reflection surface includes an aperture portion centered on the optical axis, and the aperture portion of the first reflection surface and the aperture portion of the second reflection surface are transmitting apertures that respectively transmit light.

In an ophthalmic imaging optical system according to a seventh aspect, in the ophthalmic imaging optical system according to the fourth aspect, the first reflection surface and the second reflection surface are reflectors with gas at the incidence sides thereof, and the second optical unit includes a first lens with a positive refractive power and a second lens with a negative refractive power.

In an ophthalmic imaging optical system according to an eighth aspect, in the ophthalmic imaging optical system according to the first aspect, the first optical unit and the second optical unit are respectively disposed on an optical axis of the ophthalmic imaging optical system.

In an ophthalmic imaging optical system according to a ninth aspect, in the ophthalmic imaging optical system according to the fourth aspect, the first optical unit and the second optical unit are formed so as to satisfy the conditional expression:

$$0.1 < D \cdot \tan(A/2)/S < 1.0$$

where in D represents a distance from a vertex of the refracting surface that is disposed at the side closest to the subject eye with the concave surface facing the side at which the subject eye is disposed to a center of the pupil of the subject eye, S represents a maximum effective diameter of the refracting surface in the first optical unit, and A represents an external illumination angle from the pupil.

In an ophthalmic imaging optical system according to a tenth aspect, in the ophthalmic imaging optical system according to the fourth aspect, the ophthalmic imaging optical system having the first optical unit and the second optical unit includes a lens group with a positive refractive power disposed between a fundus conjugate position that is conjugate with a fundus of the subject eye and a pupil conjugate position that is conjugate with the pupil of the subject eye, and the lens group includes at least one surface with a negative refractive power.

In an ophthalmic imaging optical system according to an eleventh aspect, in the ophthalmic imaging optical system according to the fourth aspect, the first optical unit and the second optical unit are structured in accordance with the conditional expression:

$$1 < |\beta| < 10$$

where $\beta$ represents an imaging magnification between the pupil position of the subject eye and a position of a pupil conjugate that is conjugate with the pupil position.

An ophthalmic imaging apparatus according to a twelfth aspect includes: an ophthalmic imaging optical system including a first optical unit and a second optical unit disposed on the same optical axis in this order from a side thereof at which a subject eye is disposed, the first optical unit including: a refracting surface that is disposed closest to the subject eye and is concave relative to the subject eye, a first reflection surface that includes an aperture portion at a central portion thereof containing the optical axis, and a second reflection surface that reflects light reflected from the first reflection surface to the opposite side from the side thereof at which the subject eye is disposed, and a pupil conjugate position that is conjugate with a pupil position of the subject eye with respect to the first optical unit and the second optical unit being formed at the opposite side of the subject eye: and a scanning component that is disposed at the pupil conjugate position and scans light from a light source toward the subject eye.

In an ophthalmic imaging apparatus according to a thirteenth aspect, in the ophthalmic imaging apparatus according to the twelfth aspect, the ophthalmic imaging optical system is configured to enable incident light from the pupil of the subject eye to enter into the refracting surface that is disposed at the side closest to the subject eye and is concave relative to the subject eye with at least a 100° angle of an external illumination angle, and the ophthalmic imaging optical system enables fundus imaging with an angle of at least 100°.

An optometric image acquisition method according to a fourteenth aspect is an image acquisition method for synthesizing an annular image with a circular image and acquiring a wide-angle fundus image, the optometric image acquisition method including: a first step of acquiring the circular image; a second step of acquiring the annular image; and a third step of synthesizing the circular image with the annular image and acquiring a wide-angle fundus image.

In an optometric image acquisition method according to a fifteenth aspect, in the optometric image acquisition method according to the fourteenth aspect, the circular image is imaged by a first fundus apparatus with an imaging angle of $\alpha$, and the annular image is imaged by a second fundus apparatus with an imaging angle from $\alpha$ to $\beta$ ($\alpha < \beta$).

An optometric imaging system according to a sixteenth aspect includes: a first acquisition section that acquires an annular first image of a subject eye portion imaged by the ophthalmic imaging apparatus according to the twelfth aspect; a second acquisition section that acquires a circular second image of a portion of the subject eye corresponding to an opening of an annular aperture portion; and a third acquisition section that synthesizes the annular first image acquired by the first acquisition section with the second image acquired by the second acquisition section and acquires a third image that is a synthesized wide-angle image.

DETAILED DESCRIPTION

Below, exemplary embodiments are described with reference to the attached drawings.

First Exemplary Embodiment

Figure 1:
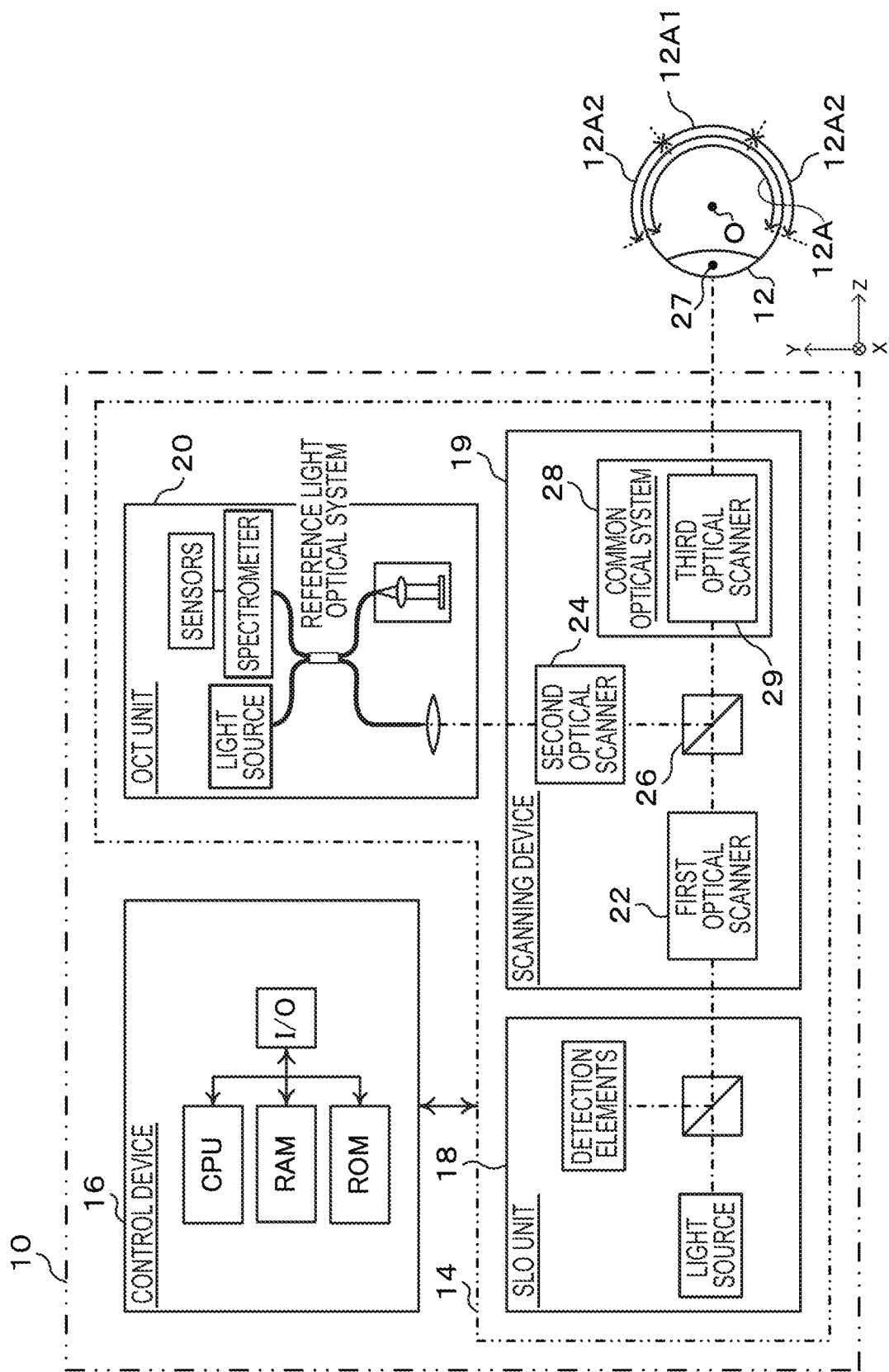
FIG. 1 is a block diagram showing an example of overall structure of an ophthalmic imaging apparatus according to a first exemplary embodiment.

FIG. 1 shows an example of structure of an ophthalmic imaging apparatus 10 according to the present exemplary embodiment.

As shown in FIG. 1, the ophthalmic imaging apparatus 10 includes an apparatus main body 14, which images the fundus of a subject eye, and a control device 16. In the descriptions below, the meaning of the term "imaging" is intended to include a user using the ophthalmic imaging apparatus 10 to acquire an image showing a subject body, for which the term "capturing an image" may be used. The apparatus main body 14 operates under the control of the control device 16. The apparatus main body 14 includes an SLO unit 18, a scanning device 19 and an OCT unit 20.

In the descriptions below, a horizontal direction when the ophthalmic imaging apparatus 10 is placed on a horizontal surface is referred to as "the X direction", a direction perpendicular to the horizontal direction is referred to as "the Y direction", and a direction from an anterior portion of a subject eye 12 through the eyeball center O toward the fundus is referred to as "the Z direction". Thus, the X direction is a direction that is orthogonal to both the Y direction and the Z direction.

As an example of principal functions that can be implemented by the ophthalmic imaging apparatus 10, the ophthalmic imaging apparatus 10 according to the present exemplary embodiment features two functions. A first function is a function that causes the ophthalmic imaging apparatus 10 to operate as a scanning laser ophthalmoscope (SLO) and capture images by SLO imaging (below referred to as "the SLO imaging system function"). The second function is a function that causes the ophthalmic imaging apparatus 10 to operate as an optical coherence tomography (OCT) apparatus and capture images by OCT imaging (below referred to as "the OCT imaging system function").

The SLO imaging system function is implemented by, among structures of the ophthalmic imaging apparatus 10, the control device 16, the SLO unit 18 and the scanning device 19, which includes a first optical scanner 22. The SLO unit 18 includes a light source, detection elements and so forth, and is capable of imaging the fundus of the subject eye 12. That is, by operating as the SLO imaging system function, the ophthalmic imaging apparatus 10 images a subject body that is (for example, an imageable region 12A of) the fundus of the subject eye 12. More specifically, light from the SLO unit 18 (below referred to as SLO light) is passed through the pupil of the subject eye 12 by the scanning device 19 and is scanned relative to the imageable region 12A in the Y direction (a vertical direction) by the first scanner 22 and in the X direction (a horizontal direction) by a third scanner 29, and an image of reflected light is acquired by the SLO unit 18. The SLO imaging system function is a widely known function. Accordingly, the SLO imaging system function is not described in detail here.

The OCT imaging system function is implemented by the control device 16, the OCT unit 20 and the scanning device 19, which includes a second optical scanner 24. The OCT unit 20 includes a light source, a spectrometer, sensors, an illuminating optical system and so forth, and is capable of imaging plural tomographic regions in the tissue thickness direction of the fundus. That is, by operating as the OCT imaging system function, the ophthalmic imaging apparatus 10 images tomographic regions that are regions in the tissue thickness direction of the fundus (for example, of the imageable region 12A). More specifically, light from the OCT unit 20 (below referred to as measurement light) is passed through the pupil of the subject eye 12 by the scanning device 19 and is scanned relative to the imageable region 12A in the Y direction (the vertical direction) by the second scanner 24 and in the X direction (the horizontal direction) by the third scanner 29. Reflected light of the measurement light is interfered with reference light to produce interference light. The OCT unit 20 detects spectral components of the interference light, and the control device 16 uses the detection results to acquire physical quantities (for example, a tomography image) representing a tomographic region. The OCT imaging system function is a widely known function. Accordingly, the OCT imaging system function is not described in detail here.

In the following descriptions, because the SLO light and the measurement light are both scanned two-dimensionally in the X direction and the Y direction, where there is no need to distinguish between the SLO light and the measurement light, the SLO light and the measurement light are collectively referred to as "scanned light".

In the present exemplary embodiment, an example of the ophthalmic imaging apparatus 10 including functions that utilize scanned light is described. However, the ophthalmic imaging apparatus featuring functions that utilize scanned light is not limiting; it is sufficient to include functions that enable observation of the subject eye 12. For example, illumination of scanned light is not limiting; an ophthalmic imaging apparatus featuring a function that illuminates light onto the fundus of the subject eye 12 and enables fundus observation of the subject eye 12 is applicable. That is, the use of reflected light from the subject eye 12 when scanned light is scanned thereon is not limiting; a function that simply illuminates light to observe the subject eye 12 may be featured. Furthermore, illumination of light onto the subject eye 12 is not limiting. For example, a function that utilizes light generated in the subject eye 12, such as fluorescent light or the like, to observe the subject eye 12 may be featured. Thus, the concept of light for observing the subject eye 12 includes light reflected from the fundus and light generated at the fundus, and is referred to as "light from the subject eye 12".

Now, an illumination angle of luminous flux relative to the subject eye 12 at the ophthalmic imaging apparatus 10 according to the present exemplary embodiment is described.

Figure 2:
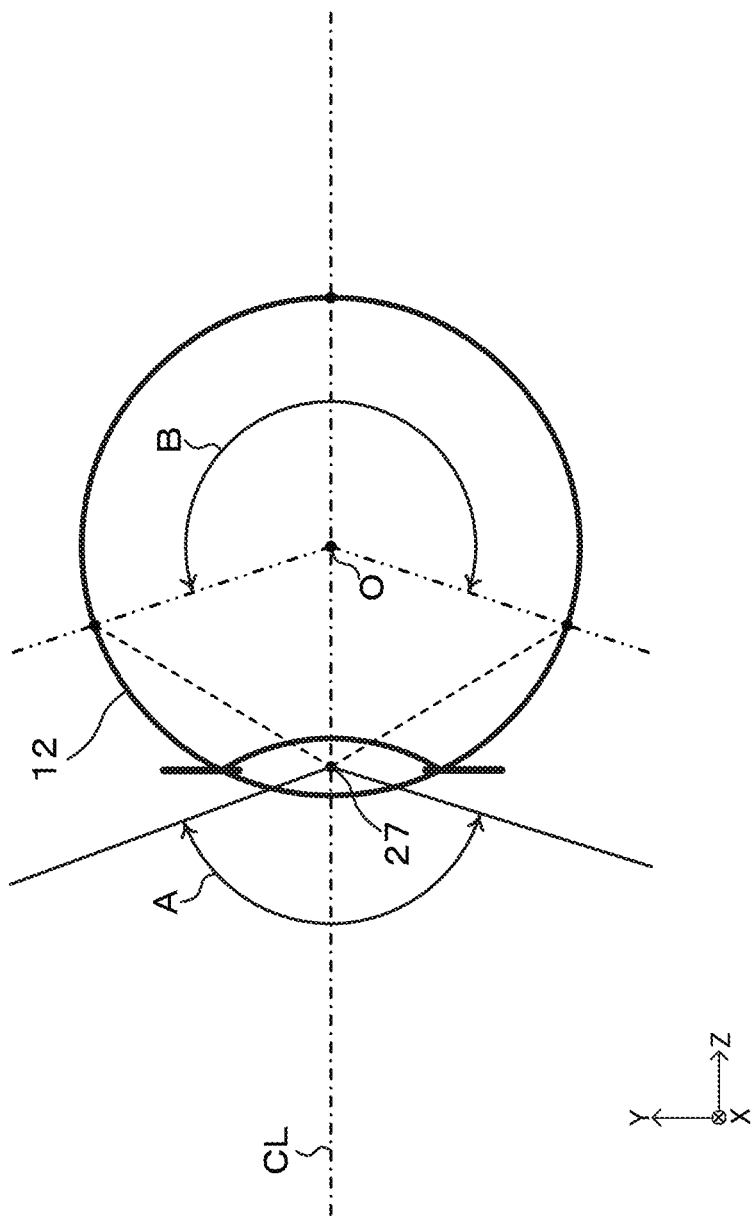
FIG. 2 is a conceptual image showing an example of an illumination angle of a subject eye at the ophthalmic imaging apparatus according to the first exemplary embodiment.
Figure 3:
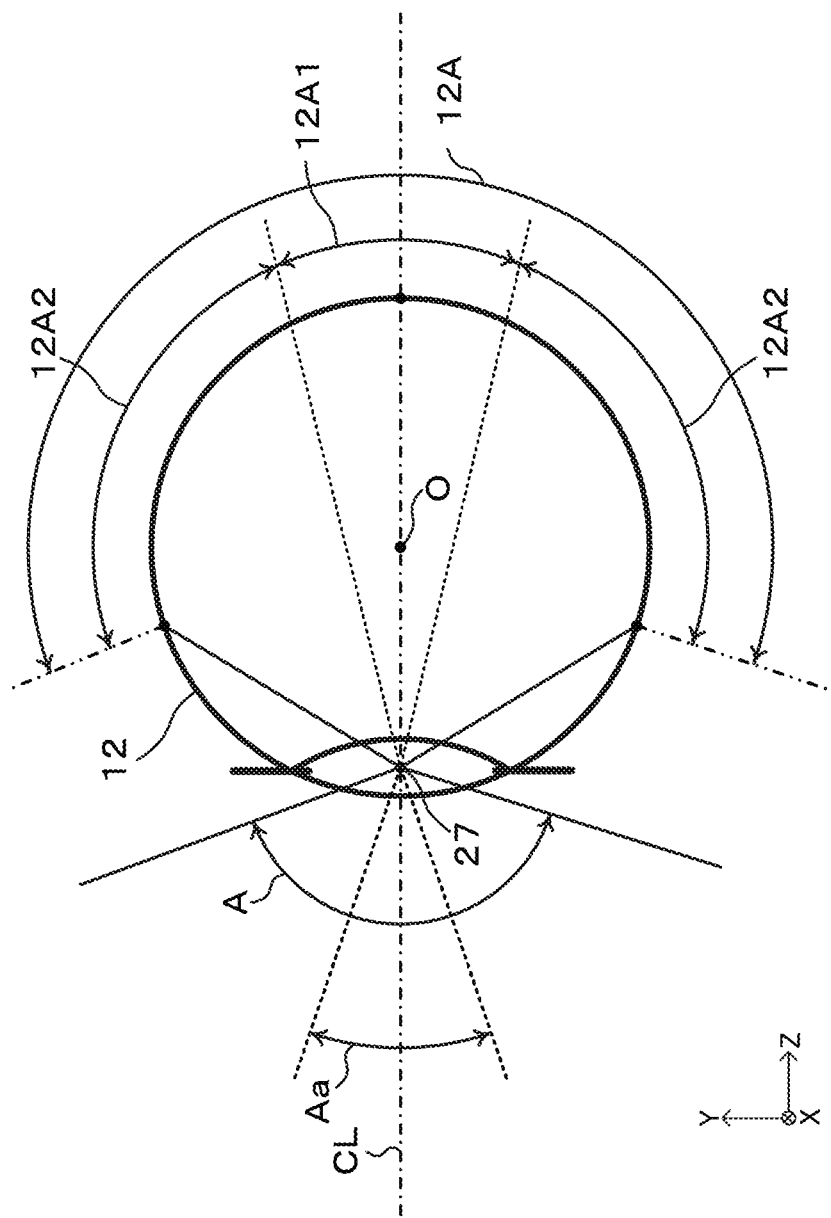
FIG. 3 is a conceptual image showing an example of an imageable region of a fundus at the ophthalmic imaging apparatus according to the first exemplary embodiment.

FIG. 2 shows an example of the illumination angle of the subject eye by the ophthalmic imaging apparatus 10 according to the present exemplary embodiment. FIG. 3 shows an example of an imageable region of the fundus.

When the fundus of the subject eye 12 is being observed, a fundus region with a greater range may be observed by making a field of view (FOV) for an observer observing the fundus, which is to say a field of view of the fundus, a wider angle. In order to observe the fundus region, in the ophthalmic imaging apparatus 10 according to the present exemplary embodiment, the fundus of the subject eye 12 is scanned with the scanned light and the fundus of the subject eye 12 is imaged. Therefore, the field of view of the fundus corresponds to the illumination angle of the scanned light. That is, it is apparent that the greater the extent of light provided to the subject eye 12, the greater the fundus region that can be imaged. Light being scanned onto the fundus is illuminated toward the center of the pupil of the subject eye 12. Because of refraction in the cornea of the subject eye, illuminated light from the ophthalmic apparatus illuminates the fundus across a somewhat narrower angle inside the subject eye. FIG. 2 schematically shows illuminated light rays from the ophthalmic apparatus in states that are refracted at the center of the pupil. Thus, it is necessary to distinguish between an external illumination angle A of light illuminated from the outside by the ophthalmic apparatus and an internal illumination angle B of illuminated light inside the subject eye that is being illuminated.

The external illumination angle A is the light illumination angle from the ophthalmic imaging apparatus 10 side, that is, from outside the subject eye 12. That is, an angle across which illuminated light toward the fundus of the subject eye 12 approaches a pupil center point 27 of the subject eye 12 (that is, a central point in an elevation view of the pupil) serves as the external illumination angle A. The external illumination angle A is equal to an angle across which light reflected from the fundus is emitted from the subject eye 12 toward the ophthalmic imaging apparatus 10, through the pupil center point 27. The internal illumination angle B represents a light illumination angle across the fundus of the subject eye 12 that is illuminated by the scanned light and effectively imaged, using the eyeball center O of the subject eye 12 as a reference point. The external illumination angle A and the internal illumination angle B are in correspondence with one another. In the descriptions below, because the ophthalmic apparatus is being described, the external illumination angle A is used as an illumination angle corresponding to the field of view of the fundus. Where the internal illumination angle is also mentioned in the descriptions below, it is given for reference.

Thus, as illustrated in FIG. 3, the ophthalmic imaging apparatus 10 images inside the imageable region 12A, which is a fundus region of the subject eye 12, in accordance with the external illumination angle A. The imageable region 12A is, for example, a maximum region that can be scanned with the scanned light by the scanning device 19. The imageable region 12A is, far example, a range that provides a field of view corresponding to an external illumination angle A of about 120°, which corresponds to an internal illumination angle of around 160°.

The imageable region 12A may be broadly divided into, for example, a first imageable region 12A1 and a second imageable region 12A2. The first imageable region 12A1 is the range of a field of view according to an external illumination angle Aa, in the vicinity of a visual axis CL that passes through the pupil center point 27 and the center O of the subject eye 12. The second imageable region 12A2 is a region surrounding the first imageable region 12A1, which is the range of a peripheral field of view that is more distant from the visual axis CL. The external illumination angle Aa corresponding to the first imageable region 12A1 is, for example, about 30° (corresponding to an internal illumination angle B of around 45°), and the external illumination angle A corresponding to the second imageable region 12A2 is, for example, about 120° (corresponding to an internal illumination angle of around 160°).

The scanning device 19 includes a common optical system 28 that is equipped with the first optical scanner 22, the second optical scanner 24, a dichroic mirror 26 and the third optical scanner 29. The first optical scanner 22, the second optical scanner 24 and the dichroic mirror 26 are disposed such that an optical path length between the first optical scanner 22 and the dichroic mirror 26 matches an optical path length between the second optical scanner 24 and the dichroic mirror 26. The common optical system 28 is used in common for both the SLO light and the illuminating light. The common optical system 28 includes the third optical scanner 29. The first optical scanner 22, the second optical scanner 24 and the third optical scanner 29 are disposed at positions that are conjugate with a central portion of the pupil of the subject eye 12. Including the dichroic mirror 26 in the common optical system is conceivable because the dichroic mirror 26 is used in common by both scanners.

In the present exemplary embodiment, a polygon mirror is used as an example of the first optical scanner 22, and a mirror galvanometer is used as an example of the second optical scanner 24. It is sufficient that the first optical scanner 22 and the second optical scanner 24 are optical elements that are capable of deflecting luminous flux in predetermined directions.

Figure 4:
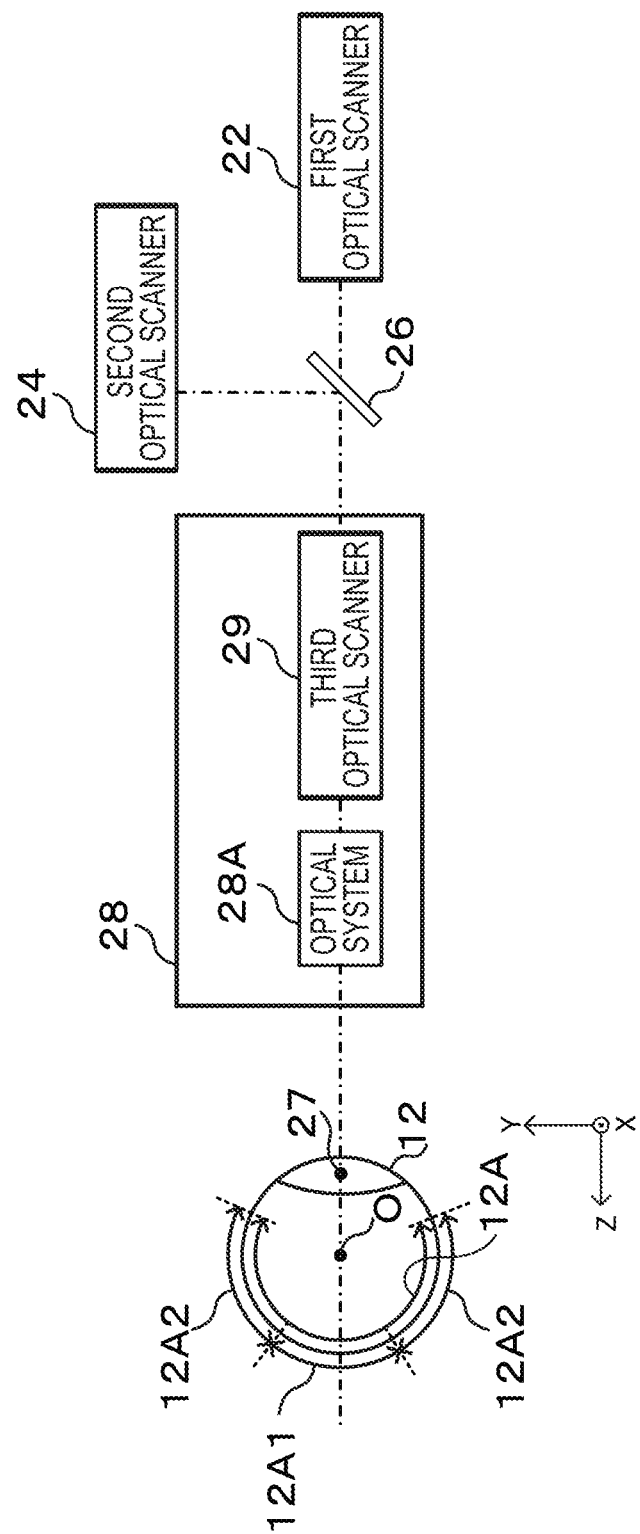
FIG. 4 is a schematic structural diagram showing an example of a scanning device included in the ophthalmic imaging apparatus according to the first exemplary embodiment.

FIG. 4 shows an example of the scanning device 19 including principal structures of the common optical system 28.

As shown in FIG. 4, the common optical system 28 includes the optical system 28A and the third optical scanner 29.

The first optical scanner 22 sends the SLO light from the SLO unit 18 to the dichroic mirror 26. The first optical scanner 22 scans the SLO light in the Y direction. This scanning of the SLO light in the Y direction is implemented by operation of a light-deflecting element such as a polygon mirror or the like. The dichroic mirror 26 transmits the SLO light sent from the first optical scanner 22 and guides the SLO light to the common optical system 28. In the common optical system 28, the SLO light is emitted from the third optical scanner 29 into the optical system 28A. The third optical scanner 29 scans the SLO light in the X direction. The scanning of the SLO light in the X direction is implemented by operation of a light-deflecting element such as a mirror galvanometer or the like.

In the common optical system 28, the SLO light from the third optical scanner 29 passes through the optical system 28A, and is incident on the pupil of the subject eye 12. The SLO light is reflected by the imageable region 12A. The reflected SLO light follows the same optical path as the SLO light in the opposite direction and reaches the SLO unit 18.

The second optical scanner 24 sends the measurement light from the OCT unit 20 to the dichroic mirror 26. The second optical scanner 24 scans the measurement light in the Y direction. This scanning of the measurement light in the Y direction is implemented by operation of a light-deflecting element such as a mirror galvanometer or the like. The dichroic mirror 26 reflects the measurement light sent from the second optical scanner 24 and guides the measurement light to the common optical system 28. In the common optical system 28, the measurement light is emitted from the third optical scanner 29 into the optical system 28A. The third optical scanner 29 scans the measurement light in the X direction.

In the common optical system 28, the measurement light from the third optical scanner 29 passes through the optical system 28A, and is incident on the pupil of the subject eye 12. The measurement light is incident on the imageable region 12A and is scattered in directions different from the tissue thickness direction of the imageable region 12A or reflected. Reflected measurement light that is obtained as a result follows the same optical path as the measurement light in the opposite direction and reaches the OCT unit 20.

As illustrated in FIG. 1, the control device 16 controls operations of the apparatus main body 14 by exchanging various kinds of information with the apparatus main body 14. The control device 16 may be realized by a computer including a central processing unit (CPU), ROM and random access memory (RAM). The control device 16 is not limited to structures including a computer and may be realized by alternative hardware structures. On the basis of signals from the SLO unit 18, the control device 16 generates a two-dimensional image 12G representing the imageable region 12A. The two-dimensional image 12G is a flat image representing a planar view of the imageable region 12A. On the basis of signals from the OCT unit 20, the control device 16 also generates tomography images of the fundus of the subject eye 12, which is to say tomographic images of the interior of the imageable region 12A.

Figure 5:
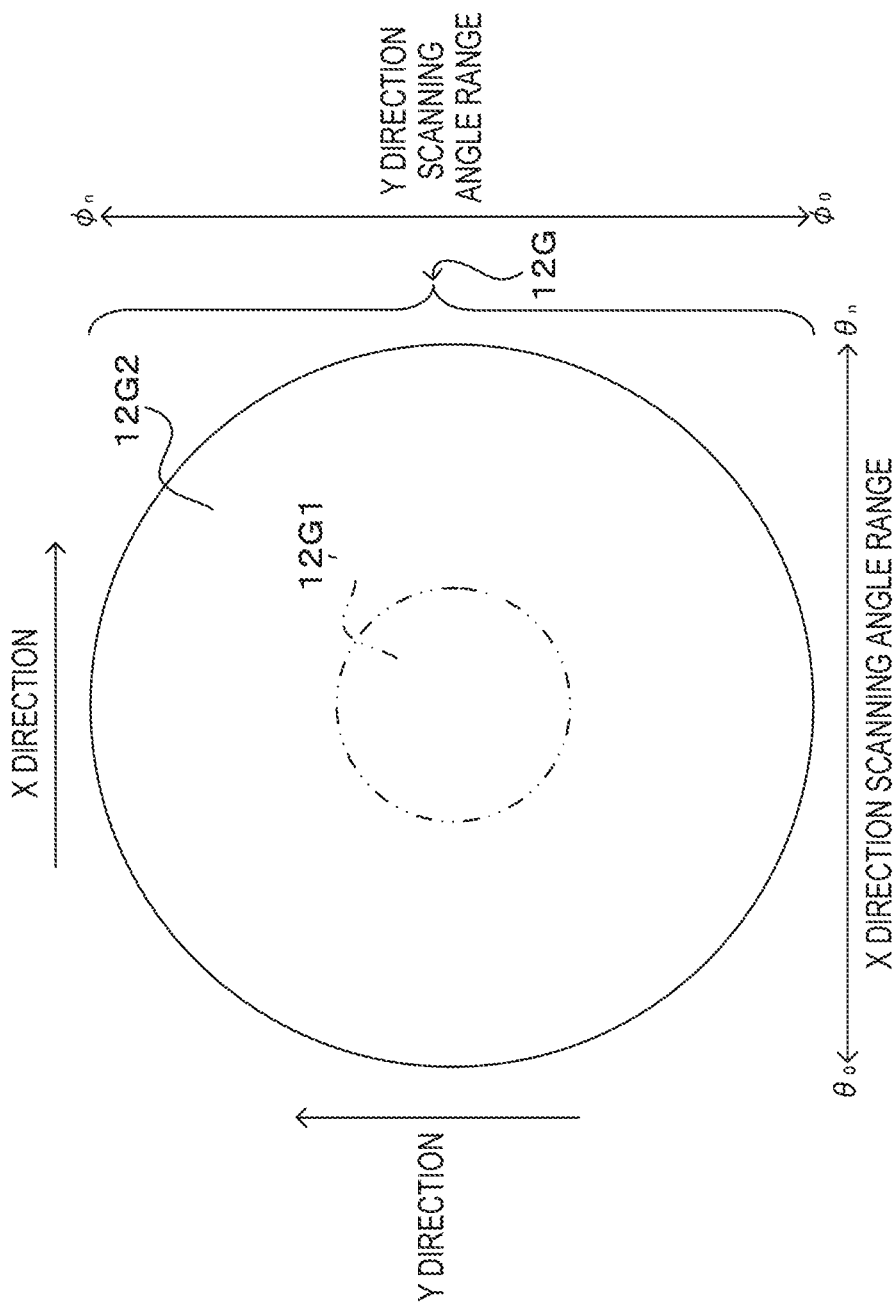
FIG. 5 is a conceptual image showing an example of a two-dimensional image acquired by the ophthalmic imaging apparatus according to the first exemplary embodiment.

FIG. 5 shows an example of the two-dimensional image 12G representing the imageable region 12A that is generated by the control device 16.

As shown in FIG. 5, an X direction scanning angle range is the range of the scanning angle of the scanned light in the X direction. In FIG. 5, as an example, the X direction scanning angle range is a range from $\theta 0°$ at least to $\theta n°$ at most. A Y direction scanning angle range is the scanning angle of the scanned light in the Y direction. In FIG. 5, as an example, the Y direction scanning angle range is a range from $\varphi 0°$ at least to $\varphi n°$ at most.

As shown in FIG. 5, the two-dimensional image 12G is broadly divided into a circular first fundus image region 12G1 that corresponds with the first imageable region 12A1 (see FIG. 3) and an annular second fundus image region 12G2 that corresponds with the second imageable region 12A2 (see FIG. 3). It is not easy to obtain images of the first fundus image region 12G1 and the second fundus image region 12G2 with high accuracy from the same scan.

That is, with the ophthalmic imaging apparatus 10 it is necessary to image a wide range in the imageable region 12A of the fundus of the subject eye 12. However, if the optical system 28A is configured using only lenses, the external illumination angle A at the subject eye 12 is an ultrawide angle and it is difficult to obtain a wider field of view. This is because it is necessary to address a number of problems, such as assuring a working distance WD between the subject eye 12 and an optical system surface that is closest to the subject eye 12, improving aberration characteristics in order to obtain high resolution images, suppressing flares and ghosts, keeping down the size and weight of the apparatus main body, and moderating fabrication difficulty and costs. These problems may come into conflict in accordance with attempts to obtain a wider field of view.

Accordingly, in the present exemplary embodiment, a catadioptric optical system combining reflective surfaces and lenses is used as a whole optical system, which may suppress occurrences of chromatic aberration and enable a reduction in size of the optical system. In consideration of these points, a wider angle corresponding to the surroundings of a fundus central portion may be observed. That is, in the present exemplary embodiment, the annular second fundus image region 12G2 corresponding to the second imageable region 12A2 (see FIG. 3) is imaged, enabling observation of the surroundings of the fundus central portion with a wider external illumination angle A. In the descriptions below, descriptions are given centering on the fundus imaging apparatus that images the fundus of the subject eye 12. However, the apparatus is not limited to observing the fundus but, by appropriate selection of positional relationships with the subject eye 12 in accordance with the optical configuration mentioned above, is also effective when observing the cornea portion of a subject eye or the like.

Figure 6:
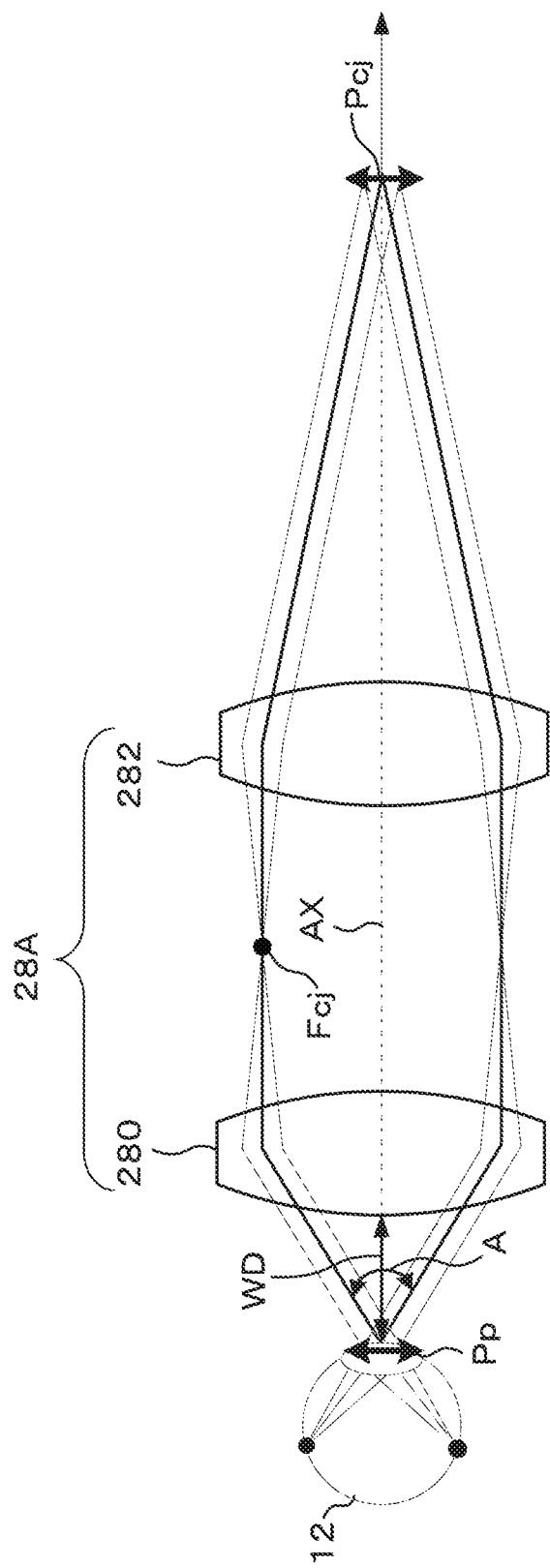
FIG. 6 is a schematic diagram of an optical system of a common optical system included in the ophthalmic imaging apparatus according to the first exemplary embodiment.

FIG. 6 schematically shows the optical system 28A of the common optical system 28, which is capable of realizing the wider angle.

As shown in FIG. 6, the optical system 28A includes a first optical unit 280 and a second optical unit 282. It is not easy to increase the working distance WD between the subject eye 12 and the optical system of the optical system 28A with lenses alone. However, in the present exemplary embodiment, reflective surfaces and lenses are utilized. The reflective surfaces have annular effective reflection regions in donut shapes with transmission apertures at the centers of the reflective surfaces. Thus, it is possible to form a wide peripheral field of view in an annular shape. Furthermore, an image of an ultrawide-angle region has satisfactory aberration characteristics, and an optical system with few occurrences of flares and ghosts, small size, and a small number of structural lenses is possible.

Figure 7:
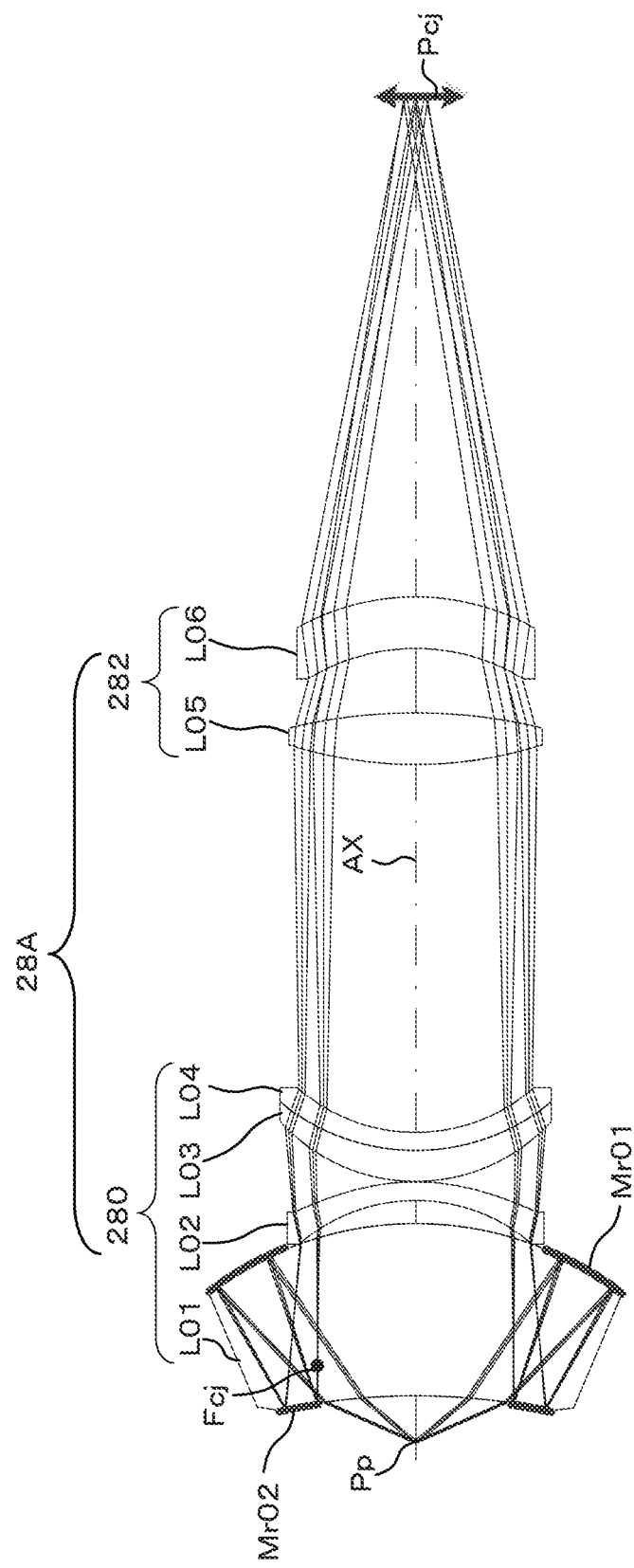
FIG. 7 is a structural diagram showing an example of a lens configuration of an optical system according to a first practical example.

Now, the optical system 28A is described in detail in accordance with FIG. 7, which is an example of the exemplary embodiment.

The first optical unit 280 is disposed at the side of the optical system 28A at which the subject eye is disposed. In the order in which light is incident in the first optical unit 280 from the side at which the pupil Pp of the subject eye 12 is disposed, spreading of luminous flux of the light from the subject eye 12 is suppressed by a first refracting face, at which a concave surface faces toward the subject eye, and subsequently the light from the subject eye 12 is reflected toward the subject eye 12 and converged by a first reflection surface including a central aperture (an annular concave reflecting mirror). Then, at a second reflection surface (an annular convex reflecting mirror), the light is reflected to the opposite direction from the direction toward the subject eye 12, and passes through the central aperture of the first reflection surface. The second optical unit 282 constituted of lenses forms light from the subject eye that is emitted from the first optical unit 280 into a pupil conjugate Pcj image in a space at the opposite side of the second optical unit 282 from the side thereof at which the subject eye is disposed, at a position that is conjugate with the position of the pupil Pp of the subject eye 12. In this optical configuration, the structure of the whole optical system may be reduced in size by forming the first reflection surface in a concave shape and the second reflection surface in a convex shape. A satisfactory working distance WD is assured and a reduction in size of the first reflection surface is enabled by the first refracting face whose concave surface faces to the side thereof at which the subject eye is disposed, and luminous flux splitting is enabled by the light being transmitted through the aperture portions of the second reflection surface and the first reflection surface.

In the optical system with this configuration, disposing a lens group with a positive refractivity between a fundus conjugate image Fcj position that is conjugate with the fundus of the subject eye and the pupil conjugate image Pcj position that is conjugate with the pupil of the subject eye, and including at least one face with a negative refractivity in this lens group, is effective for correcting aberrations.

Back-face reflective surfaces that are integral structures formed at the surfaces at both sides of a medium with a refractive index greater than 1 are employed as the first reflection surface including a central aperture and the second reflection surface including a central aperture. Thus, it is possible to realize both assurance of a longer working distance WD and formation with smaller reflecting mirrors.

When this optical system 28A is configured so as to satisfy the conditions in the following expression (1), it is possible both to have a longer working distance WD and to obtain a large field of view with a small optical system.

$$0.1 < D \cdot \tan(A/2)/S < 1.0 \tag{1}$$

In this expression, D represents a distance from the position of the pupil Pp of the subject eye 12 to the first refracting face, S represents a maximum effective diameter of the refracting face in the optical system, and A represents the external illumination angle, which is the external illumination angle onto the position of the pupil.

It is preferable if the upper limit in expression (1) is 0.9 and the lower limit is 0.2.

The ophthalmic imaging apparatus 10 according to the present exemplary embodiment features the SLO imaging system function and the OCT imaging system function, each of which functions requires scanning imaging at high speed and satisfactory resolution. These requirements may be met by forming the optical system 28A so as to satisfy the conditions in the following expression (2).

$$1 < |\beta| < 10 \tag{2}$$

In this expression, β represents an imaging magnification between the pupil position of the subject eye 12 and the position of the pupil conjugate that is conjugate with the pupil position. It is more preferable if the lower limit in the above expression (2) is greater than 2.

Comatic aberration of the pupil between the pupil Pp of the subject eye 12 and the pupil conjugate Pcj causes a difference in the luminous flux angle of a fundus image at the pupil conjugate Pcj image position, which leads to a change in resolving power at the fundus position. In order to correct this comatic aberration of the pupil, it is preferable to dispose a lens group with a positive refractivity overall between the fundus conjugate Fcj position that is conjugate with the fundus of the subject eye 12 and the pupil conjugate Pcj position, and to configure a face with a negative refractivity at at least one surface in this lens group. Even more preferably, the imaging magnification β in expression (2) may be modified by a distortion factor M of the maximum field of view when an aplanatic ideal lens is included at the pupil conjugate Pcj position, as expressed by the following expression (3). In this case, the upper limit becomes 17.0 and the lower limit becomes 9.0.

$$|\beta|/(1-M) \tag{3}$$

First Practical Example

FIG. 7 shows an example of a lens configuration of the optical system 28A of the ophthalmic imaging apparatus 10 according to a first practical example.

The optical system 28A includes the first optical unit 280. In the first optical unit 280, a positive meniscus lens L01, a negative meniscus lens L02, a positive meniscus lens L03 and a negative meniscus lens L04 are combined in a lens composition arrayed in this order from the side thereof at which the pupil Pp of the subject eye 12 is disposed. A concave surface of the positive meniscus lens L01 faces to the side at which the pupil Pp is disposed. A concave surface of the negative meniscus lens L02 faces to the side at which the pupil Pp is disposed and includes an aspherical shape. A convex surface of the positive meniscus lens L03 faces to the side at which the pupil Pp is disposed. The optical system 28A also includes the second optical unit 282 at a light emission side of the first optical unit 280. In the second optical unit 282, a convex lens L05 and a meniscus lens L06 are arrayed in this order from the side thereof at which the pupil Pp of the subject eye 12 is disposed. A concave surface of the meniscus lens L06 faces to the side at which the pupil Pp is disposed.

All of the optical elements constituting the optical system 28A, which is to say the optical elements included in the first optical unit 280 (the lenses L01, L02, L03 and L04) and the optical elements included in the second optical unit 282 (the lenses L05 and L06), are arranged along a single optical axis AX.

Parallel luminous flux from the subject eye 12 that is emitted from the first optical unit 280 diverges slightly before entering the succeeding second optical unit 282. The second optical unit 282 includes two lenses and converts weakly divergent light from the first optical unit 280 to parallel luminous flux. Thus, depending on the configuration with the first optical unit 280, the second optical unit 282 forms a conjugate image of the pupil Pp of the subject eye 12 in a space at the opposite side of the second optical unit 282 from the side thereof at which the subject eye 12 is disposed.

In this configuration, the light rays shown in FIG. 7 represent a situation in which parallel luminous flux emitted from the pupil position Pp of the subject eye 12 is formed by the optical system 28A at the pupil conjugate position Pcj in the space at the opposite side of the optical system 28A from the side at which the subject eye 12 is disposed. In this case, assuming that light from the fundus is emitted from the subject eye 12 as parallel luminous flux, the conjugate position of the fundus of the subject eye 12 is at the position marked as point Fcj in FIG. 7, which represents a primary spatial image of the fundus being formed between an annular concave reflection surface Mr01 and an annular convex reflection surface Mr02. Obviously, respective illumination beams (laser lights) from the SLO unit 18 and OCT unit 20 described above are incident on the subject eye 12 at various angles (that is, the external illumination angle) in the form of parallel luminous flux centered on the pupil position Pp of the subject eye 12. The same applies in the practical examples described below.

Imaging characteristics may be further improved by forming the surfaces in aspherical surface shapes as appropriate.

These aspherical surfaces are represented by the following expression (4), in which a height in a direction perpendicular to the optical axis is represented by r, a distance along the optical axis from a plane tangential to a vertex of the spherical surface to a position of the aspherical surface at height r (a sag quantity) is represented by z, the reciprocal of a vertex curvature radius is represented by c, a conic coefficient is represented by k, and nth-order aspherical surface coefficients are represented by A, B, C, D and E.

$$z=(c \cdot r^2)/[1+\{1-(1+k) \cdot r^2 \cdot c^2\}^{1/2}]+A \cdot r^4+B \cdot r^6+C \cdot r^8+D \cdot r^{10}+E \cdot r^{12} \quad (4)$$

The following Table 1 shows values of elements of the optical system 28A according to the first practical example.

Table 1 represents a situation in which the effective field of view angle (the external illumination angle A from the pupil) is 100°-132° (a first surface incidence angle of 50°-66°) and the working distance WD is 18 mm. The overall length (a distance L2 from the pupil Pp position of the subject eye 12 to the pupil conjugate Pcj position) is 520.88 mm, and the pupil imaging magnification β from the pupil Pp position to the pupil conjugate Pcj position is 4.9×. A distortion factor M1 (a distortion factor of the maximum field of view at the fundus conjugate Fcj when an aplanatic ideal lens is included at the pupil conjugate Pcj position) is 0.574.

TABLE 1

| Surface Number | Lens Number | Radius of curvature (mm) | Surface separation (mm) | Refractive index Nd, dispersion Vd | Effective radius (mm) |
|---|---|---|---|---|---|
| Subject eye | | ∞ | ∞ | | |
| 1 (pupil surface) | D | ∞ | 18.00000 | | 1.00 |
| 2 | L01 | −242.47210 | 66.68069 | 1.48749, 70.3 | 35.55 |
| 3 | First reflection surface | −129.74184 | −66.68069 | 1.48749, 70.3 | 76.74 |
| 4 | Second reflection surface | −242.47210 | 66.68069 | 1.48749, 70.3 | 50.23 |
| 5 | | −129.74184 | 8.92625 | | 44.51 |
| 6 | L02 | −67.79268 | 7.20000 | 1.80809, 22.7 | 44.44 |
| 7 (aspherical surface) | | −86.34353 | 0.20000 | | 47.11 |
| 8 | L03 | 70.00000 | 12.00000 | 1.69680, 55.5 | 50.00 |
| 9 | L04 | 81.43144 | 7.00000 | 1.86074, 23.1 | 47.82 |
| 10 | | 68.11664 | 142.49494 | | 44.79 |
| 11 | L05 | 158.55076 | 20.00000 | 1.49782, 82.6 | 46.63 |
| 12 | | −204.58045 | 24.91431 | | 45.92 |
| 13 | L06 | −78.78320 | 20.00000 | 1.80809, 22.8 | 40.92 |
| 14 Pupil conjugate | | −92.55391 | 193.46853 | | 43.71 |

The aspherical surface coefficients representing the aspherical surface of surface 7 at lens L02 are as follows.

A=+0.398342E−06
B=−0.976217E−10
C=−0.544603E−13

Figure 8:
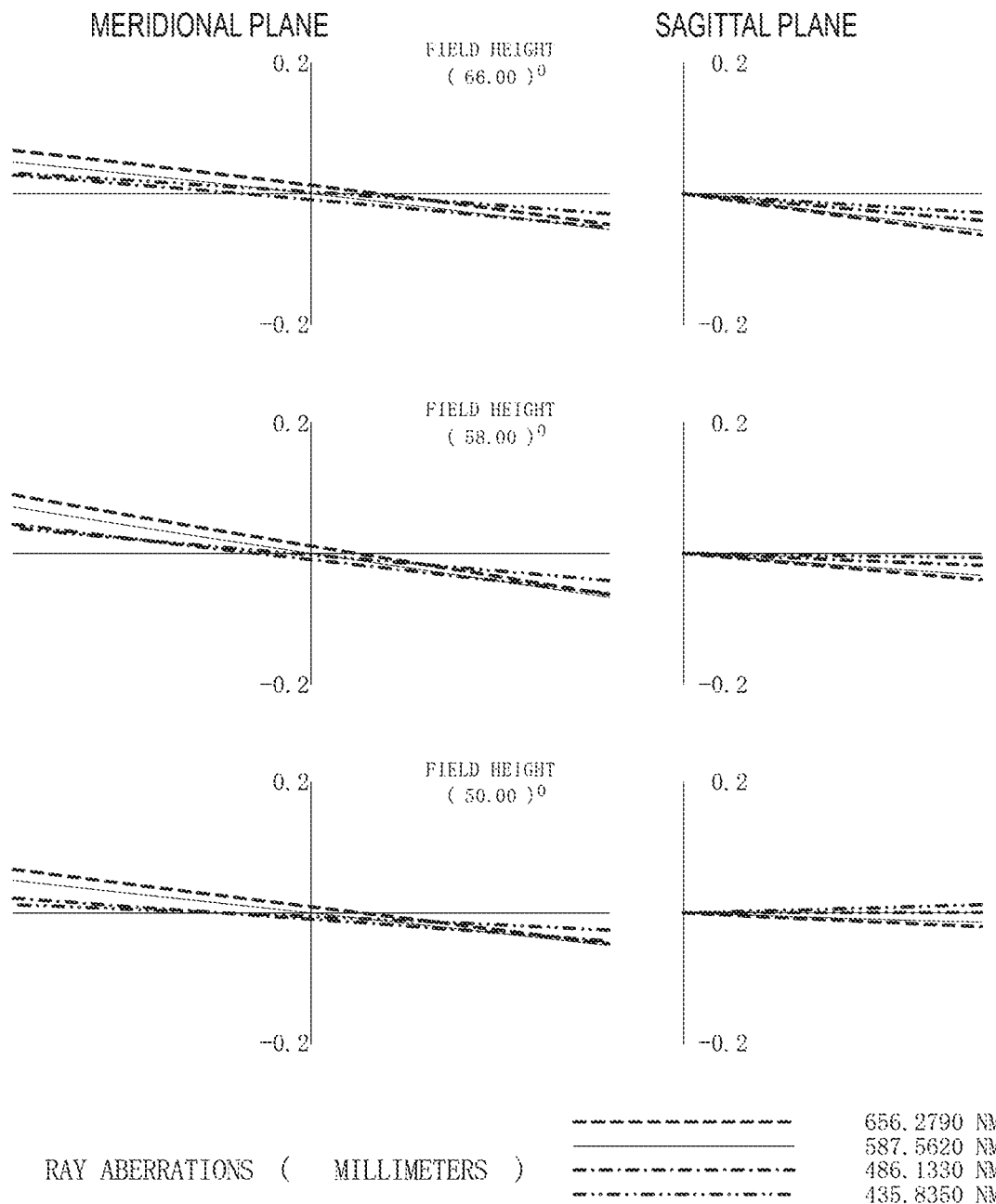
FIG. 8 is a lateral aberration diagram of the optical system according to the first practical example.

FIG. 8 shows lateral aberration diagrams of the optical system 28A configured in accordance with the elements in Table 1. These lateral aberration diagrams are aberration diagrams of fundus images when an aplanatic ideal lens is suitably included at the pupil conjugate Pcj position, for evaluation of optical characteristics of the present practical example. Similarly in the practical examples described below, an aplanatic ideal lens is included and aberrations are calculated.

In the aberration diagrams shown in FIG. 8, the vertical axis represents image height. The solid line represents a central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 8, in the optical system 28A according to the first practical example, variations in aberration for lights in the visible wavelength region are suppressed and are excellently corrected. It can also be seen that the optical system 28A corrects excellently in the vicinity of the effective field of view (that is, the external illumination angle A) from 100° to 132° (the first surface incidence angle of) 50°-66°. This corresponds to an internal illumination angle of approximately 130°-165°. Although not shown in the drawings, it can be verified that various other aberrations such as spherical aberration, astigmatism, distortion aberration and the like are also excellently corrected.

Second Practical Example

The second practical example is a variant example of the first practical example. The second practical example widens the effective viewing angle (i.e., the external illumination angle A).

The second practical example has a similar structure to the first practical example. Accordingly, structures that are the same are assigned the same reference symbols and are not described in detail here. The optical system 28A, which is different, is described.

Figure 9:
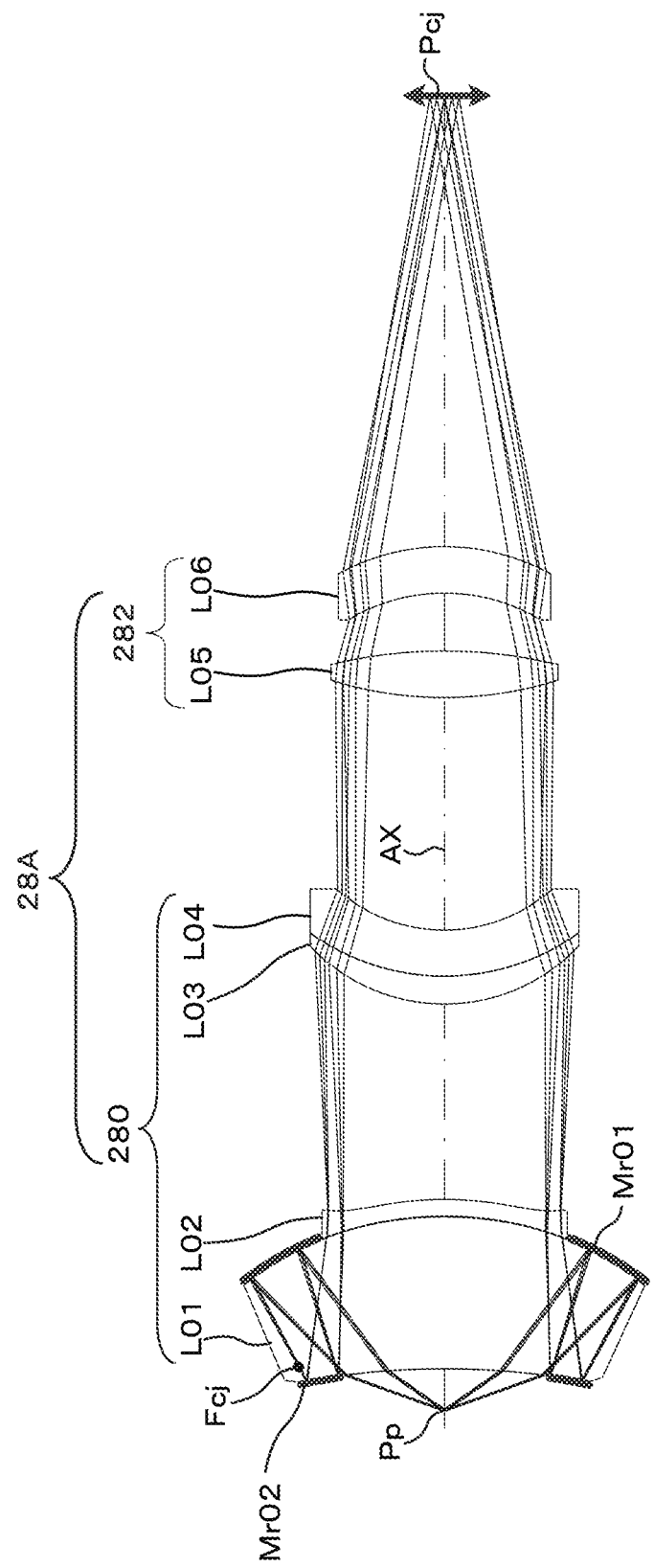
FIG. 9 is a structural diagram showing an example of a lens configuration of an optical system according to a second practical example.

FIG. 9 shows a lens configuration of the optical system 28A of the ophthalmic imaging apparatus 10 according to the second practical example.

The optical system 28A according to the second practical example includes the first optical unit 280, in which a positive meniscus lens L01, a negative meniscus lens L02, a positive meniscus lens L03 and a negative meniscus lens L04 are combined in a lens composition arrayed in this order from the side thereof at which the pupil Pp of the subject eye 12 is disposed. A concave surface of the positive meniscus lens L01 faces to the side at which the pupil PP is disposed. A concave surface of the negative meniscus lens L02 at the side thereof at which the pupil Pp is disposed includes an aspherical surface shape that is mated with the light emission side of the positive meniscus lens L01. A convex surface of the positive meniscus lens L03 faces to the side at which the pupil Pp is disposed. The optical system 28A also includes a second optical unit with the same lens configuration as the second optical unit 282 shown in FIG. 7.

The same as in the first practical example, all of the optical elements constituting the optical system 28A (the lenses L01, L02, L03 and L04 and the lenses L05 and L06) are arranged along the single optical axis AX.

The following Table 2 shows values of elements of the optical system 28A according to the second practical example.

Table 2 represents a situation in which the effective field of view angle (the external illumination angle A from the pupil) is 110°-140° (a first surface incidence angle of 55°-70°) and the working distance WD is 18 mm. The overall length (the distance L2 from the pupil Pp position of the subject eye 12 to the pupil conjugate Pcj position) is 565 mm, and the pupil imaging magnification β from the pupil Pp position to the pupil conjugate Pcj position is 3.92×. A distortion factor M2 (a distortion factor of the maximum field of view at the fundus conjugate Fcj when the aplanatic ideal lens is included at the pupil conjugate Pcj position) is 0.720.

TABLE 2

| Surface Number | Lens Number | Radius of curvature (mm) | Surface separation (mm) | Refractive index Nd, dispersion Vd | Effective radius (mm) |
|---|---|---|---|---|---|
| Subject eye | | ∞ | ∞ | | |
| 1 (pupil surface) | D | ∞ | 18.00000 | | 1.00 |
| 2 | L01 | −329.21730 | 65.36435 | 1.48749, 70.3 | 42.78 |
| 3 (aspherical surface) | First reflection surface | −151.86751 | −65.36435 | 1.48749, 70.3 | 82.74 |
| 4 | Second reflection surface | −329.21730 | 65.36435 | 1.48749, 70.3 | 58.79 |
| 5 (aspherical surface) | | −151.86751 | 0.28342 | | 50.20 |
| 6 | L02 | −144.28176 | 7.20000 | 1.80809, 22.7 | 50.06 |
| 7 (aspherical surface) | | −128.90042 | 83.99201 | | 49.57 |
| 8 | L03 | 77.49241 | 12.00000 | 1.69680, 55.5 | 55.00 |
| 9 | L04 | 97.02421 | 19.77738 | 1.86074, 23.1 | 53.25 |
| 10 | | 68.16000 | 100.00000 | | 45.35 |
| 11 | L05 | 158.55076 | 20.00000 | 1.49782, 82.6 | 46.28 |
| 12 | | −204.58045 | 24.91431 | | 45.54 |
| 13 | L06 | −78.78320 | 20.00000 | 1.80809, 22.8 | 40.47 |
| 14 First pupil conjugate | | −92.55391 | 193.46853 | | 43.17 |

The aspherical surface coefficients representing the aspherical surface of surface 3 at lens L01 and surface 5 are as follows.

A=−0.902137E−07

B=+0.794263E−11

C=−0.318956E−15

The aspherical surface coefficients representing the aspherical surface of surface 7 at lens L02 are as follows.

A=+0.585897E−06

B=−0.983043E−10

C=+0.117076E−12

D=−0.125282E−16

Figure 10:
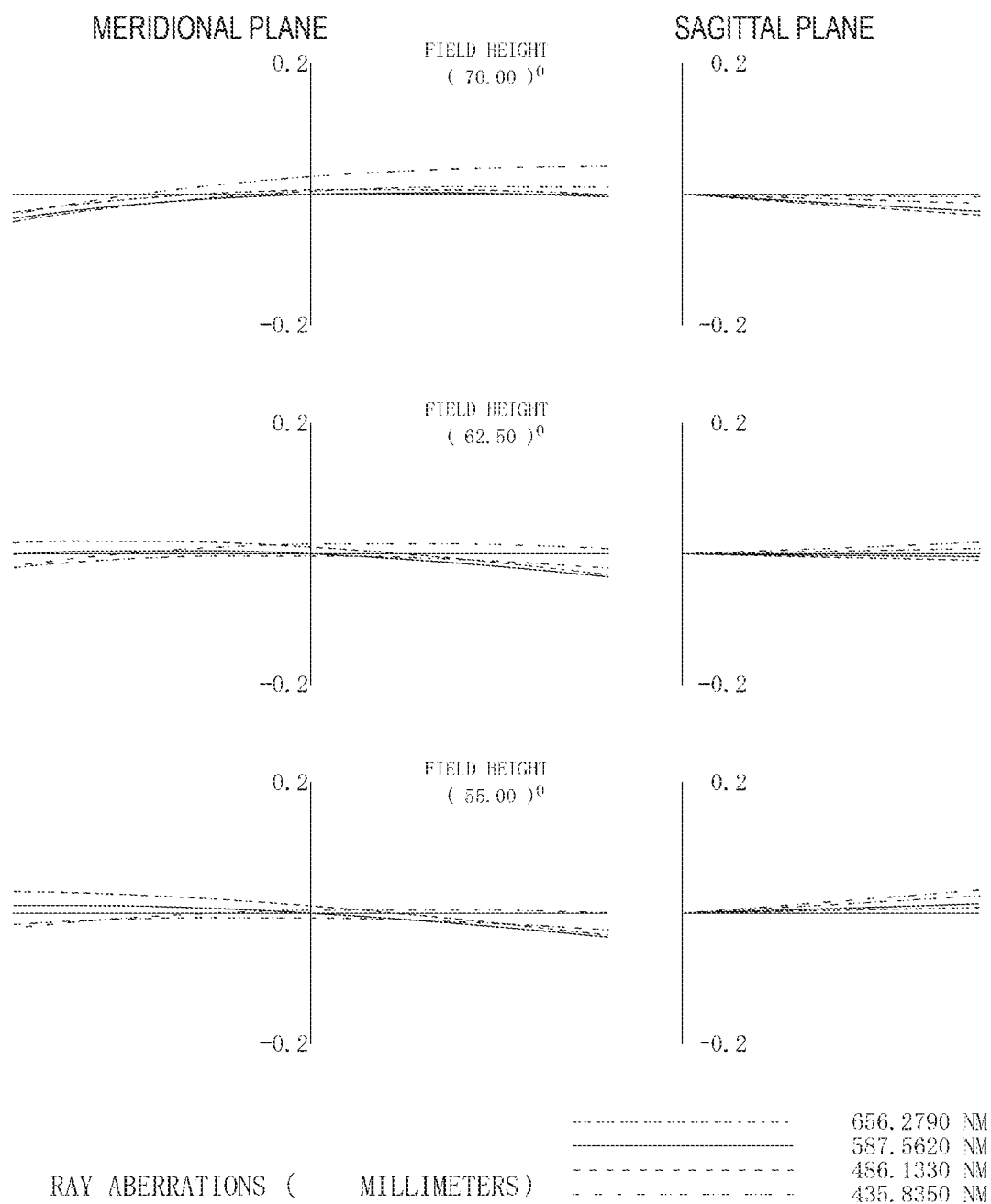
FIG. 10 is a lateral aberration diagram of the optical system according to the second practical example.

FIG. 10 shows lateral aberration diagrams of the optical system 28A configured in accordance with the elements in Table 2.

In the aberration diagrams shown in FIG. 10, the same as in the first practical example, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 10, in the optical system 28A according to the second practical example, variations in aberration for lights in the visible wavelength region are suppressed and are excellently corrected. It can also be seen that the optical system 28A corrects excellently in the vicinity of the effective field of view at 140° (the first surface incidence angle of 70°). This corresponds to an internal illumination angle of approximately 180°. Although not shown in the drawings, it can be verified that various other aberrations such as spherical aberration, astigmatism, distortion aberration and the like are also excellently corrected.

Third Practical Example

The third practical example is a variant example of the first practical example.

The third practical example has a similar structure to the first practical example. Accordingly, structures that are the same are assigned the same reference symbols and are not described in detail here.

Figure 11:
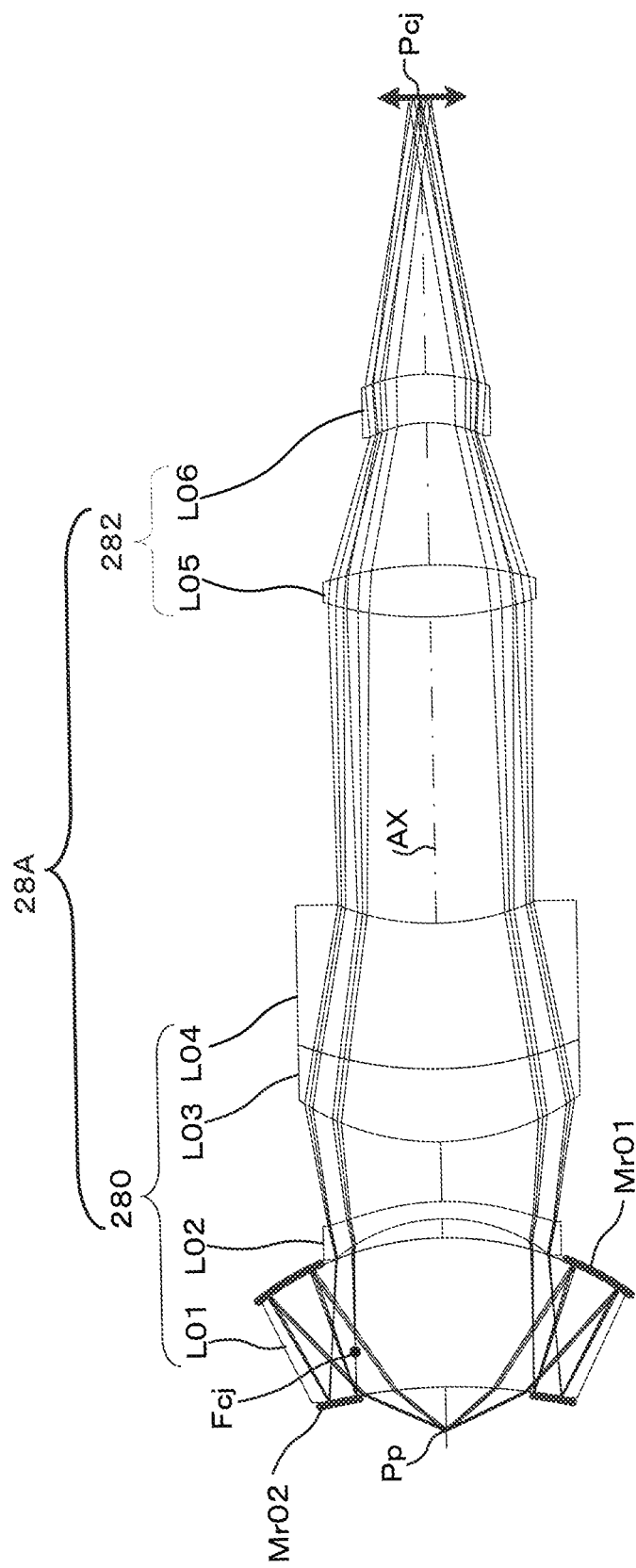
FIG. 11 is a structural diagram showing an example of a lens configuration of an optical system according to a third practical example.

FIG. 11 shows a lens configuration of the optical system 28A of the ophthalmic imaging apparatus 10 according to the third practical example.

The optical system 28A according to the third practical example includes the first optical unit 280, in which a positive meniscus lens L01, a negative meniscus lens L02, a positive meniscus lens L03 and a negative meniscus lens L04 are combined in a lens composition arrayed in this order from the side thereof at which the pupil Pp of the subject eye 12 is disposed. A concave surface of the positive meniscus lens L01 faces to the side at which the pupil Pp is disposed. A concave surface of the negative meniscus lens L02 at the side at which the pupil Pp is disposed includes an aspherical surface shape. A convex surface of the positive meniscus lens L03 faces to the side at which the pupil Pp is disposed. An optical system at the light emission side of the first optical unit 280 includes the second optical unit 282. In the second optical unit 282, at the light emission side of the first optical unit 280, a convex lens L05 and a meniscus lens L06 are arrayed in this order from the side thereof at which the pupil Pp of the subject eye 12 is disposed. A concave surface of the meniscus lens L06 faces to the side at which the pupil surface D is disposed.

All of the optical elements constituting the optical system 28A, which is to say the optical elements included in the first optical unit 280 (the lenses L01, L02, L03 and L04) and the optical elements included in the second optical unit 282 (the lenses L05 and L06), are arranged along the single optical axis AX.

The following Table 3 shows values of elements of the optical system 28A according to the third practical example.

Table 3 represents a situation in which the effective field of view angle (the external illumination angle A from the pupil) is 100°-130° (a first surface incidence angle of 50°-65°) and the working distance WD is 18 mm. The overall length (the distance L2 from the pupil Pp position of the subject eye 12 to the pupil conjugate Pcj position) is 549.19 mm, and the pupil imaging magnification β from the pupil Pp position to the pupil conjugate Pcj position is 5.64×. The distortion factor M2 (the distortion factor of the maximum field of view at the fundus conjugate Fcj when an aplanatic ideal lens is included at the pupil conjugate Pcj position) is 0.517.

TABLE 3

| Surface Number | Lens Number | Radius of curvature (mm) | Surface separation (mm) | Refractive index Nd, dispersion Vd | Effective radius (mm) |
|---|---|---|---|---|---|
| Subject eye pupil | | ∞ | ∞ | | |
| 1 | D | ∞ | 18.00000 | | 1.00 |
| 2 | L01 | −225.23197 | 61.38739 | 1.48749, 70.3 | 34.05 |
| 3 | First reflection surface | −122.43666 | −61.38739 | 1.48749, 70.3 | 71.70 |
| 4 | Second reflection surface | −225.23197 | 61.38739 | 1.48749, 70.3 | 47.71 |
| 5 | | −122.43666 | 7.81275 | | 43.58 |
| 6 | L02 | −68.39584 | 7.20000 | 1.80809, 22.7 | 43.52 |
| 7 (aspherical surface) | | −98.42014 | 24.67075 | | 46.41 |
| 8 | L03 | 99.15145 | 30.00000 | 1.69680, 55.5 | 55.00 |
| 9 | L04 | 154.32713 | 60.00000 | 1.86074, 23.1 | 51.17 |
| 10 | | 101.00880 | 126.21633 | | 39.95 |
| 11 | L05 | 140.25105 | 21.45278 | 1.49782, 82.6 | 41.43 |
| 12 | | −152.27739 | 58.59737 | | 40.51 |
| 13 | L06 | −50.61851 | 20.00000 | 1.80809, 22.8 | 22.95 |
| 14 First pupil conjugate | | −67.17169 | 113.85311 | | 24.59 |

The aspherical surface coefficients representing the aspherical surface of surface 7 at lens L02 are as follows.

A=+0.505045E−06
B=−0.185139E−09
C=+0.118203E−12
D=−0.133097E−16

Figure 12:
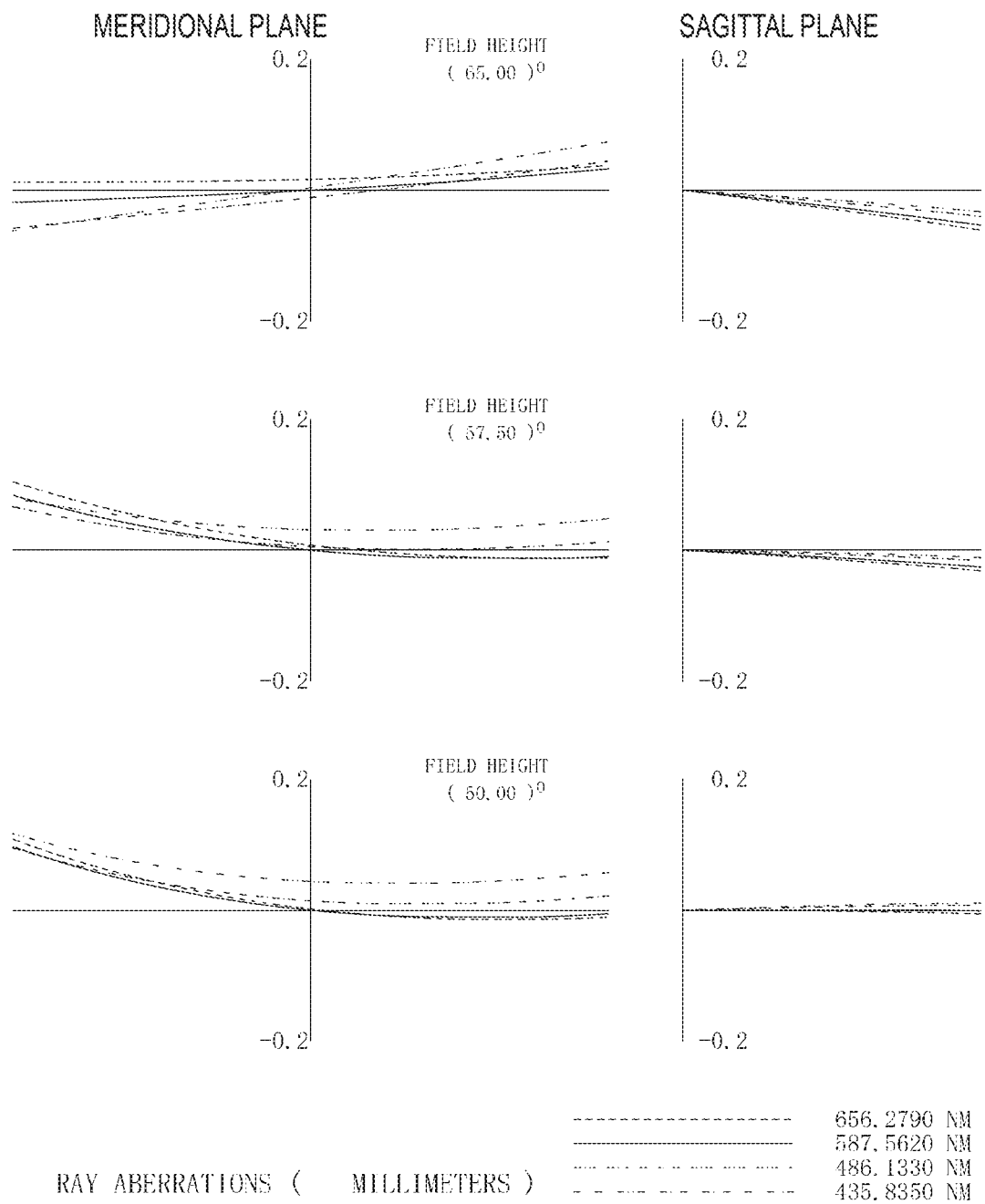
FIG. 12 is a lateral aberration diagram of the optical system according to the third practical example.

FIG. 12 shows lateral aberration diagrams of the optical system 28A configured in accordance with the elements in Table 3.

In the aberration diagrams shown in FIG. 12, the same as in the first practical example, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 12, in the optical system 28A according to the third practical example, variations in aberration for lights in the visible wavelength region are suppressed and are excellently corrected, even in the vicinity of the effective field of view at 130° (the first surface incidence angle of 65°). This corresponds to an internal illumination angle of approximately 165°. Although not shown in the drawings, it can be verified that various other aberrations such as spherical aberration, astigmatism, distortion aberration and the like are also excellently corrected.

Second Exemplary Embodiment

Structures of the second exemplary embodiment that are the same as in the first exemplary embodiment are assigned the same reference symbols and are not described in detail here.

In the second exemplary embodiment, when it is assumed both that the aperture diameter of the lens elements is to be small and that the aperture diameter of the reflection surfaces is to be small, the common optical system 28 is formed with the emphasis on reducing the aperture diameter of the lens elements. More specifically, emphasis is put on making the aperture diameter of the lens elements smaller, while an increase in size of the reflection surfaces is tolerated to some extent. In order from the side of the first optical unit 280 at which the pupil Pp of the subject eye 12 is disposed, the first optical unit 280 includes a lens with a positive refractivity of which a concave surface faces to the side thereof at which the subject eye 12 is disposed, a first reflection surface, a second reflection surface, a lens with a negative refractivity, and a lens with a positive refractivity. The first reflection surface is an annular concave reflective surface with a central aperture, and is a surface-reflecting surface with gas at the incidence side thereof. The second reflection surface is an annular convex reflective surface, which is a surface-reflecting surface with gas at the incidence side thereof. In this configuration, it is preferable to dispose the lens with a negative refractivity between the first reflection surface and the second reflection surface. Parallel luminous flux from the subject eye 12 that is emitted from the first optical unit 280 diverges slightly before entering the succeeding second optical unit 282. The second optical unit 282 includes two lenses and converts weakly divergent light from the first optical unit 280 to parallel luminous flux. Thus, depending on the configuration with the first optical unit 280, the second optical unit 282 forms a conjugate image of the pupil Pp of the subject eye 12 in a space at the opposite side of the second optical unit 282 from the side thereof at which the subject eye 12 is disposed.

Fourth Practical Example

Now, a fourth practical example according to the second exemplary embodiment is described. Structures of the fourth practical example that are the same as structures of any of the first to third practical examples are assigned the same reference symbols and are not described in detail here.

Figure 13:
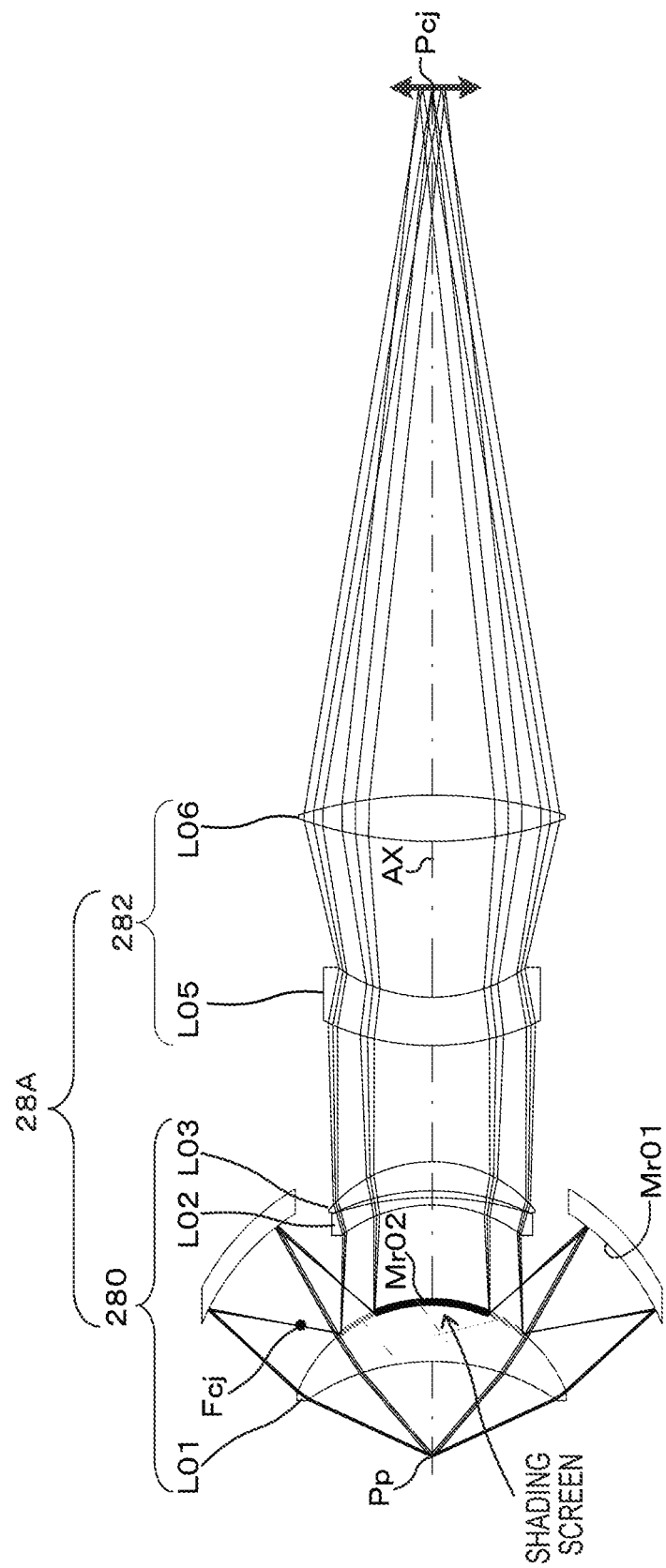
FIG. 13 is a structural diagram showing a lens configuration of an optical system according to a fourth practical example, which is an example of a second exemplary embodiment.

FIG. 13 shows a lens configuration of the optical system 28A of the ophthalmic imaging apparatus 10 according to the fourth practical example.

The optical system 28A according to the fourth practical example includes the first optical unit 280. In the first optical unit 280, a positive meniscus lens L01, an annular first reflection surface Mr01, a second reflection surface Mr02, a negative meniscus lens L02 and a positive meniscus lens L03 are arrayed in this order from the side thereof at which the pupil Pp of the subject eye 12 is disposed. A concave surface of the positive meniscus lens L01 faces to the side at which the pupil Pp is disposed. A concave surface of the first reflection surface Mr01 faces to the side at which the pupil Pp is disposed. The second reflection surface Mr02 is provided at a central portion of a convex surface of the positive meniscus lens L01. A concave surface of the negative meniscus lens L02 faces to the side at which the pupil Pp is disposed. A concave surface of the positive meniscus lens L03 faces to the side at which the pupil Pp is disposed. The optical system 28A also includes the second optical unit 282 at the light emission side of the first optical unit 280. In the second optical unit 282, a meniscus lens L05 and a positive lens L06 are arrayed in this order from the side thereof at which the pupil Pp of the subject eye 12 is disposed. A convex surface of the meniscus lens L05 faces to the side at which the pupil Pp is disposed.

All of the optical elements constituting the optical system 28A, which is to say the optical elements included in the first optical unit 280 (the lenses L01, L02 and L03) and the optical elements included in the second optical unit 282 (the lenses L05 and L06), are arranged along the single optical axis AX.

The following Table 4 shows values of elements of the optical system 28A according to the fourth practical example.

Table 4 represents a situation in which the effective field of view angle (the external illumination angle A from the pupil) is 80°-130° (a first surface incidence angle of 40°-65°) and the working distance WD is 39.1089 mm. The overall length (the distance L2 from the pupil Pp position of the subject eye 12 to the pupil conjugate Pcj position) is 565 mm, and the pupil imaging magnification β from the pupil Pp position to the pupil conjugate Pcj position is 6.4×. The distortion factor M2 (the distortion factor of the maximum field of view at the fundus conjugate Fcj when an aplanatic ideal lens is included at the pupil conjugate Pcj position) is 0.518.

TABLE 4

| Surface Number | Lens Number | Radius of curvature (mm) | Surface separation (mm) | Refractive index Nd, dispersion Vd | Effective radius (mm) |
|---|---|---|---|---|---|
| Subject eye pupil | | ∞ | ∞ | | |
| 1 | D | ∞ | 39.10890 | | 1.00 |
| 2 | L01 | −89.22313 | 24.61018 | 1.49782, 82.6 | 50.81 |
| 3 | | −59.08816 | 53.10935 | | 55.00 |
| 4 | First reflection surface | −101.99977 | −53.10935 | | 91.40 |
| 5 | Second reflection surface | −59.08816 | 40.00000 | | 37.19 |
| 6 | L02 | −60.00000 | 3.00000 | 1.76182, 26.6 | 36.36 |
| 7 | | −127.94213 | 2.86962 | | 39.09 |
| 8 | L03 | −91.58806 | 11.96633 | 1.49782, 82.6 | 39.15 |
| 9 | | −54.33130 | 48.00224 | | 40.17 |
| 10 | L05 | 100.00000 | 20.00000 | 1.80809, 22.8 | 42.26 |
| 11 | | 66.31289 | 64.36818 | | 38.00 |
| 12 | L06 | 163.38309 | 19.05397 | | 52.20 |
| 13 | | −185.81582 | 292.02062 | | 52.23 |
| First pupil conjugate | | | | | |

Figure 14:
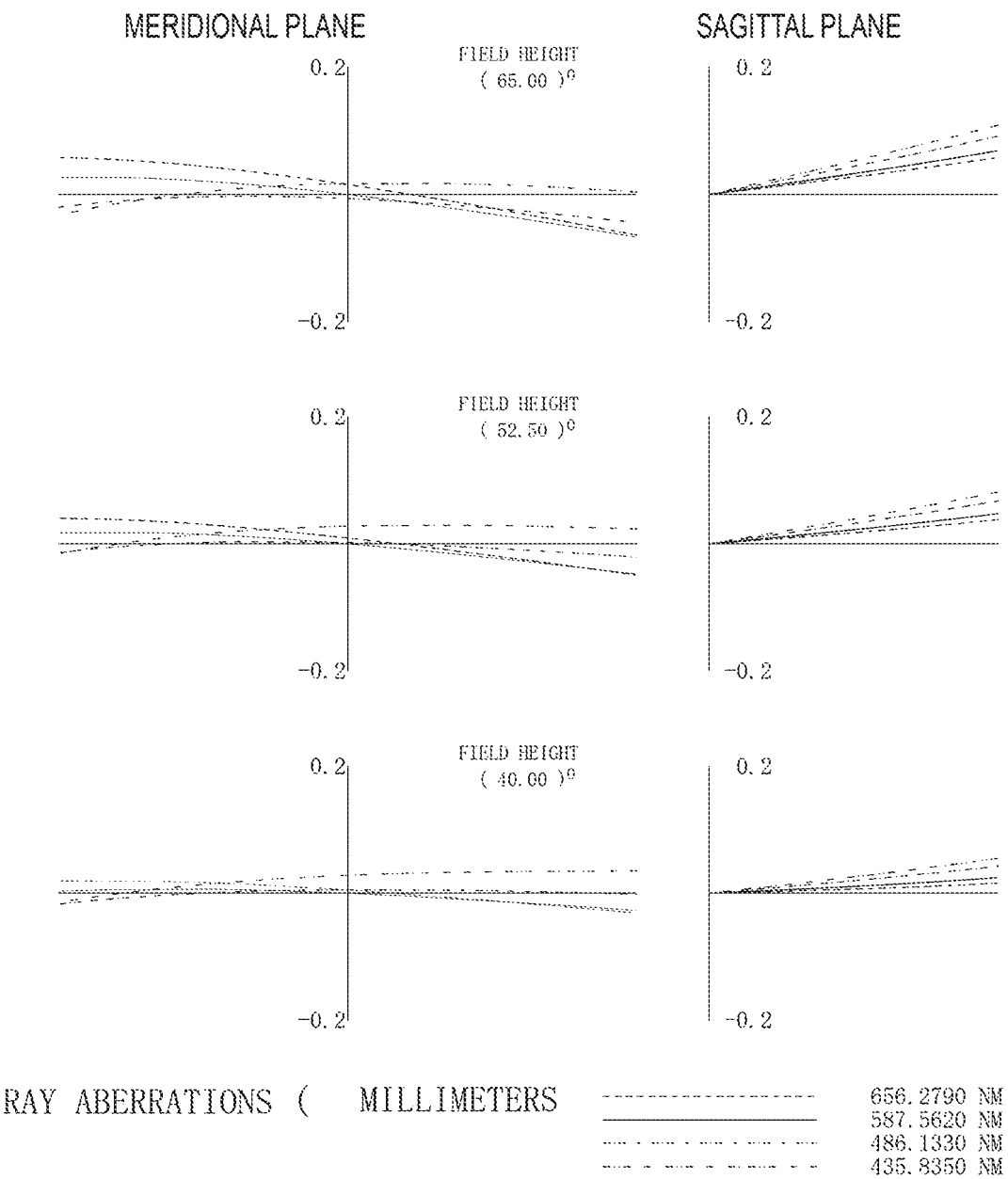
FIG. 14 is a lateral aberration diagram of the optical system according to the fourth practical example.

FIG. 14 shows lateral aberration diagrams of the optical system 28A configured in accordance with the elements in Table 4.

In the aberration diagrams shown in FIG. 14, the same as in the first practical example, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 14, in the optical system 28A according to the fourth practical example, variations in aberration for lights in the visible wavelength region are suppressed and are excellently corrected in the vicinity of the effective field of view at 100° (the first surface incidence angle of 50°). This corresponds to an internal illumination angle of approximately 135°. Although not shown in the drawings, it can be verified that various other aberrations such as spherical aberration, astigmatism, distortion aberration and the like are also excellently corrected.

Fifth Practical Example

The fifth practical example is a variant example of the fourth practical example. More specifically, the second reflection surface Mr02 of the first optical unit 280 according to the fourth practical example is provided at the central portion of the convex surface of the positive meniscus lens L01, but the fifth practical example is configured such that the second reflection surface Mr02 is provided at an element separate from a positive meniscus lens L01.

The fifth practical example has a similar structure to the fourth practical example. Accordingly, structures that are the same are assigned the same reference symbols and are not described in detail here.

Figure 15:
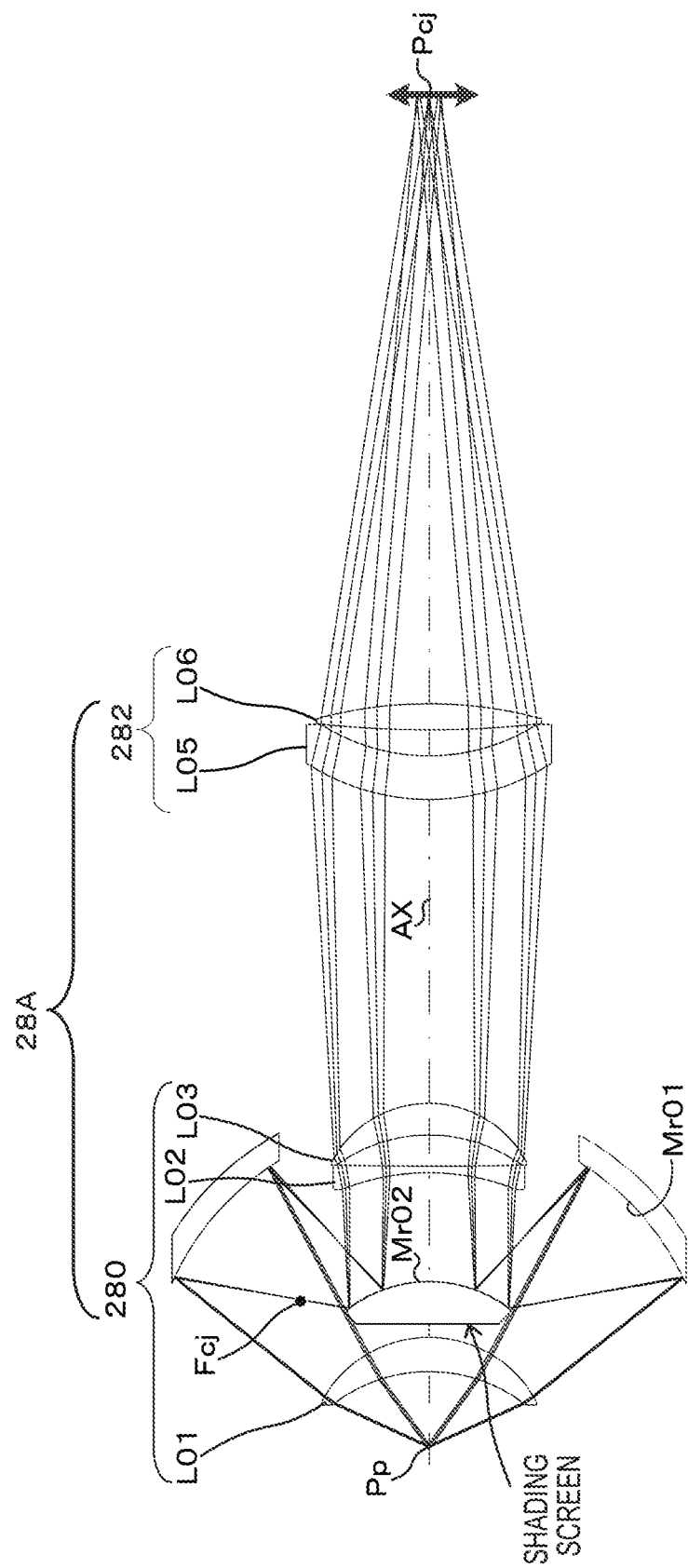
FIG. 15 is a structural diagram showing a lens configuration of an optical system according to a fifth practical example, which is an example of the second exemplary embodiment.

FIG. 15 shows a lens configuration of the optical system 28A according to the fifth practical example.

The optical system 28A according to the fifth practical example includes the first optical unit 280. In the first optical unit 280, the positive meniscus lens L01, an annular first reflection surface Mr01 including an aspherical surface shape, a second reflection surface Mr02 including an aspherical surface shape, a negative lens L02 and a positive meniscus lens L03 are arrayed in this order from the side thereof at which the pupil Pp of the subject eye 12 is disposed. A concave surface of the positive meniscus lens L01 faces to the side at which the pupil Pp is disposed. A concave surface of the first reflection surface Mr01 faces to the side at which the pupil Pp is disposed. The second reflection surface Mr02 is provided at a central portion of a convex surface at the opposite side from the side thereof at which the pupil Pp is disposed. A concave surface of the negative meniscus lens L02 faces to the side at which the pupil Pp is disposed. A concave surface of the positive meniscus lens L03 faces to the side at which the pupil Pp is disposed. The optical system 28A also includes the second optical unit 282 at the light emission side of the first optical unit 280. In the second optical unit 282, a meniscus lens L05 and a positive lens L06 are arrayed in this order from the side thereof at which the pupil Pp of the subject eye 12 is disposed. A convex surface of the meniscus lens L05 faces to the side at which the pupil Pp is disposed.

All of the optical elements constituting the optical system 28A (the lenses L01, L02 and L03 and the lenses L05 and L06) are arranged along the single optical axis AX.

The following Table 5 shows values of elements of the optical system 28A according to the fifth practical example.

Table 5 represents a situation in which the effective field of view angle (the external illumination angle A from the pupil) is 70°-130° (a first surface incidence angle of 35°-65°) and the working distance WD is 34.448 mm. The overall length (the distance L2 from the pupil Pp position of the subject eye 12 to the pupil conjugate Pcj position) is 620 mm, and the pupil imaging magnification β from the pupil Pp position to the pupil conjugate Pcj position is 7.6×. The distortion factor M2 (the distortion factor of the maximum field of view at the fundus conjugate Fcj when an aplanatic ideal lens is included at the pupil conjugate Pcj position) is 0.450. A maximum diameter of the reflection surfaces is 230 mm, and a maximum effective diameter of the refracting face is 106.3 mm.

TABLE 5

| Surface Number | Lens Number | Radius of curvature (mm) | Surface separation (mm) | Refractive index Nd, dispersion Vd | Effective radius (mm) |
|---|---|---|---|---|---|
| Subject eye pupil | | ∞ | ∞ | | |
| 1 | D | ∞ | 34.44765 | | 1.00 |
| 2 | L01 | −70.00000 | 15.66477 | 1.59319, 67.9 | 43.08 |
| 3 | | −54.42441 | 25.58099 | | 47.29 |
| 4 | Virtual surface | −58.73975 | 75.32132 | | 57.14 |
| 5 (aspherical surface) | First reflection surface | −125.75112 | −75.32132 | | 115.00 |
| 6 (aspherical surface) | Second reflection surface | −58.73975 | 50.00000 | | 36.25 |
| 7 | L02 | −104.90424 | 3.00000 | 1.76182, 26.6 | 39.11 |
| 8 | | 1633.52922 | 14.26565 | | 41.32 |
| 9 | L03 | −70.05541 | 14.52143 | 1.49782, 82.6 | 41.40 |
| 10 | | −49.23060 | 139.45870 | | 42.89 |
| 11 | L05 | 100.00000 | 20.00000 | 1.80809, 22.8 | 53.15 |
| 12 | | 89.39939 | 11.94711 | | 48.59 |
| 13 | L06 | 453.67848 | 11.97727 | 1.59319, 67.9 | 48.61 |
| 14 First pupil conjugate | | −188.86514 | 279.13644 | | 48.62 |

The aspherical surface coefficients representing the aspherical surface of surface 5 are as follows.

A=−0.119695E−08
B=+0.639162E−12
C=+0.383380E−16
D=−0.483487E−20
E=+0.121159E−24

The aspherical surface coefficients representing the aspherical surface of surface 6 are as follows.

A=−0.449100E−06
B=+0.253492E−08
C=−0.308466E−11
D=+0.171588E−14
E=−0.458747E−18

Figure 16:
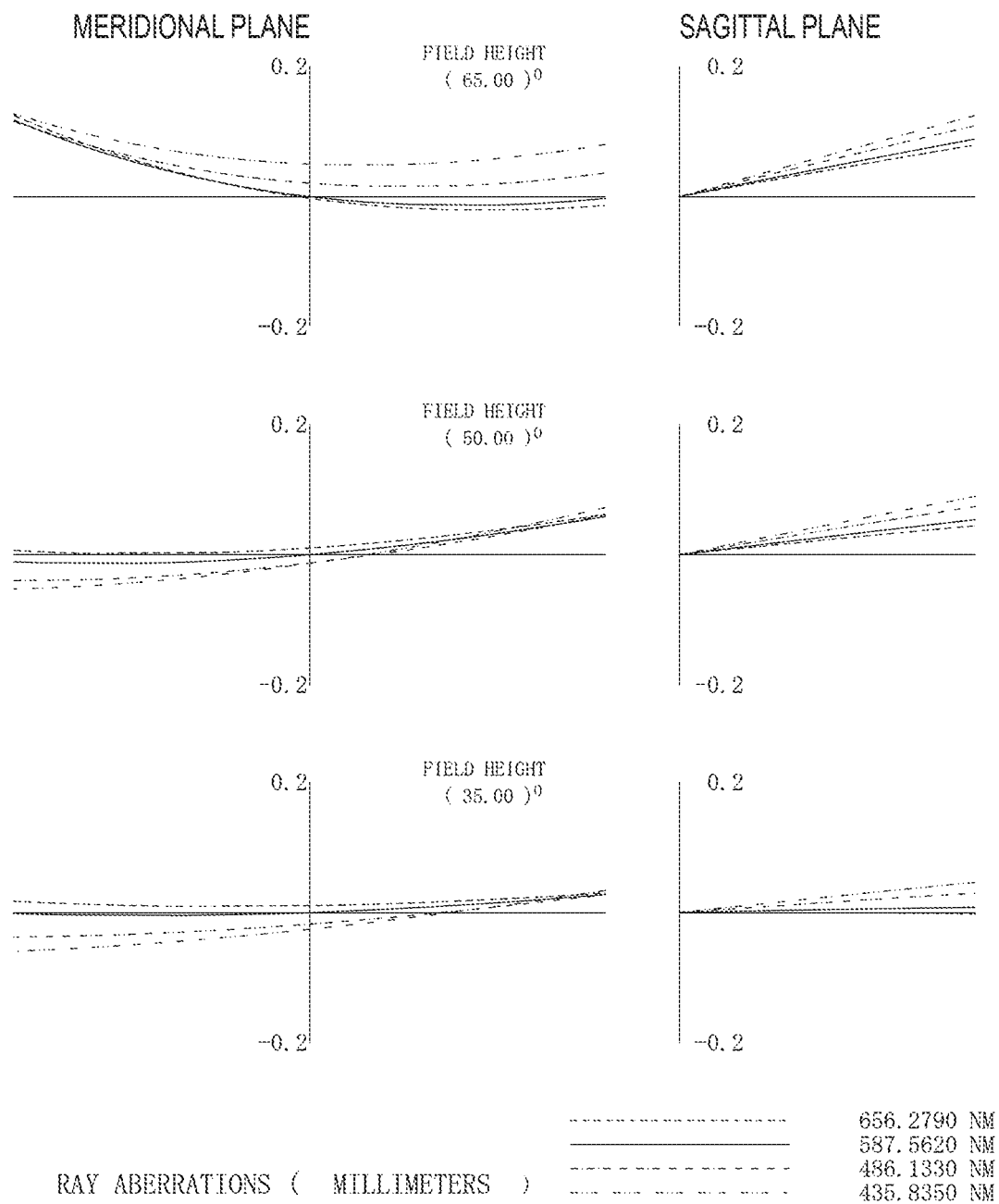
FIG. 16 is a lateral aberration diagram of the optical system according to the fifth practical example.

FIG. 16 shows lateral aberration diagrams of the optical system 28A configured in accordance with the elements in Table 5.

In the aberration diagrams shown in FIG. 16, the same as in the first practical example, the vertical axis represents image height. The solid line represents the central wavelength of 587.5620 nm, the broken line represents 656.2790 nm, the single-dot chain line represents 486.1330 nm, and the two-dot chain line represents 435.8350 nm.

As is clear from the aberration diagrams shown in FIG. 16, in the optical system 28A according to the fifth practical example, variations in aberration for lights in the visible wavelength region are suppressed and are excellently corrected. It can also be seen that the optical system 28A corrects excellently in the vicinity of the effective field of view at 130° (the first surface incidence angle of 65°). This corresponds to an internal illumination angle of approximately 165°. Although not shown in the drawings, it can be verified that various other aberrations such as spherical aberration, astigmatism, distortion aberration and the like are also excellently corrected.

The following Table 6 shows corresponding values in the conditional expressions described above for the respective configurations of the first to fifth practical examples.

TABLE 6

| Practical example | D | A | S | β | M | Conditional expression (1) | Conditional expression (2) | Conditional expression (3) |
|---|---|---|---|---|---|---|---|---|
| First practical example | 18 | 132 | 100 | 4.9 | 0.574 | 0.40 | 4.90 | 11.50 |
| Second practical example | 18 | 140 | 110 | 3.92 | 0.72 | 0.45 | 3.92 | 14.00 |
| Third practical example | 18 | 130 | 110 | 5.64 | 0.517 | 0.35 | 5.64 | 11.68 |
| Fourth practical example | 39.1089 | 130 | 110 | 6.4 | 0.518 | 0.76 | 6.40 | 13.28 |
| Fifth practical example | 34.448 | 130 | 106.3 | 7.6 | 0.45 | 0.69 | 7.60 | 13.82 |

Third Exemplary Embodiment

Structures of the third exemplary embodiment that are the same as in the first exemplary embodiment and the second exemplary embodiment are assigned the same reference symbols and are not described in detail here.

The third exemplary embodiment is an imaging system that is capable of providing images of the whole of the imageable region 12A according to the external illumination angle A that is the field of view (FOV). That is, the first exemplary embodiment and the second exemplary embodiment may provide a captured image of the surroundings of a fundus central portion around the visual axis CL, that is, the second fundus image region 12G2 corresponding to the annular second imageable region 12A2 (see FIG. 3). Accordingly, in the third exemplary embodiment, a captured image of the fundus central portion around the visual axis CL, that is, the first fundus image region 12G1 corresponding to the first imageable region 12A1 (see FIG. 3) may be acquired, and the images of the fundus center and the surroundings of the fundus central portion may be synthesized to provide the two-dimensional image 12G of the whole of the imageable region 12A.

Figure 17:
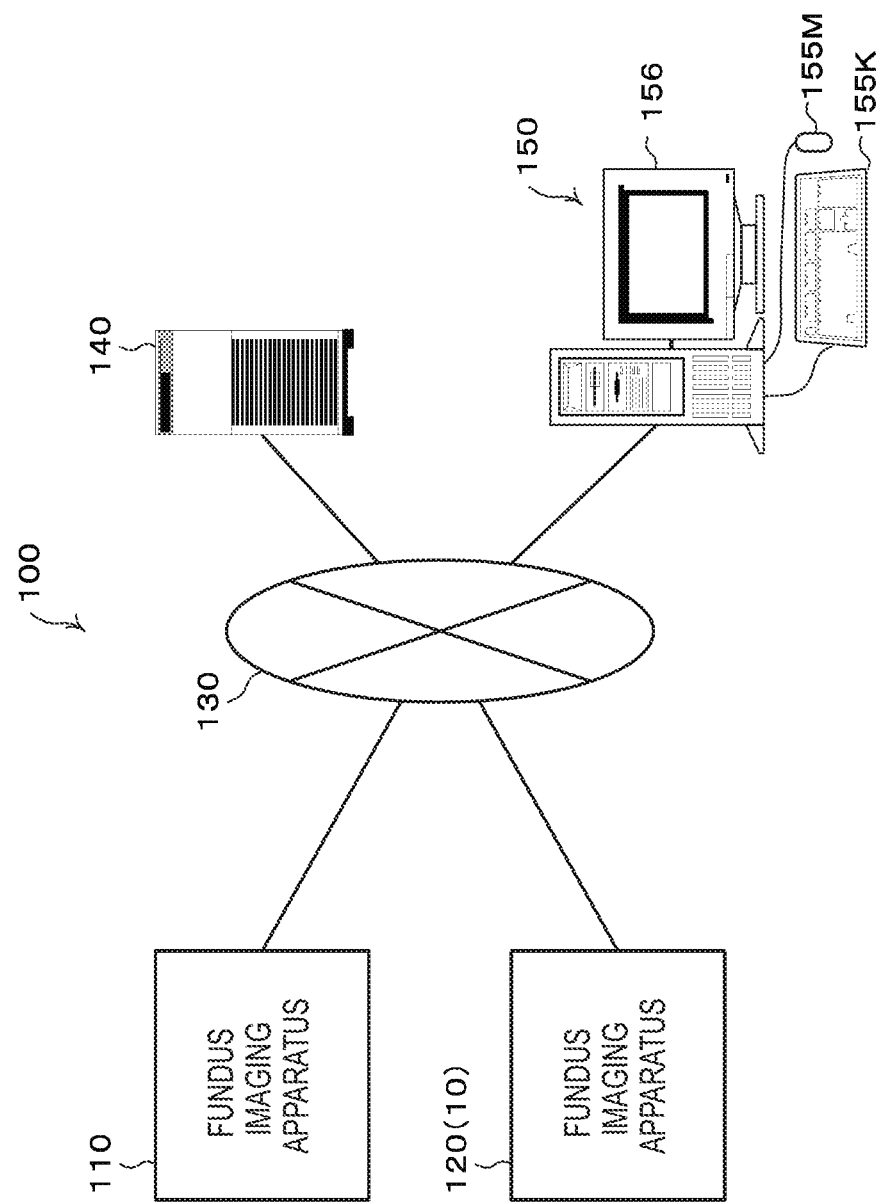
FIG. 17 is a block diagram showing an example of overall structure of an imaging system according to a third exemplary embodiment.

FIG. 17 shows the imaging system 100, which serves as an example of the imaging system according to the third exemplary embodiment that may provide an image of the whole of the imageable region 12A. The imaging system 100 is provided with a first ophthalmic imaging apparatus 110, a second ophthalmic imaging apparatus 120, a network 130 such as the Internet, a local area network or the like, an image server 140, and an image display terminal 150.

The imaging system 100 includes the first ophthalmic imaging apparatus 110, which provides images of the fundus central portion around the visual axis CL. The imaging system 100 includes the ophthalmic imaging apparatus 10 according to either of the first exemplary embodiment and second exemplary embodiment, including the practical examples, as the second ophthalmic imaging apparatus 120, which images the surroundings of the fundus central portion around the visual axis CL and obtains surrounding images. The first ophthalmic imaging apparatus 110 and second ophthalmic imaging apparatus 120 are connected to the network 130. The image server 140 and image display terminal 150 are also connected to the network 130.

The first ophthalmic imaging apparatus 110 images, for example, a fundus region from 0° to 30° with an imaging angle centered on the visual axis CL, that is, an external illumination angle of 30°. By use of the SLO unit of the first ophthalmic imaging apparatus 110, a fundus image of a circular region with an imaging angle of 15° centered on the visual axis CL may be obtained. By use of the OCT unit, OCT-3D volume data of a circular region with an imaging angle (that is, external illumination angle) of 30° centered on the visual axis CL may be obtained, and 3D data analyses and various maps may be created. Retinal tomography images may also be obtained by use of the OCT unit.

The second ophthalmic imaging apparatus 120 images, for example, a fundus region from 30° to 100° with an imaging angle centered on the visual axis CL, that is, an external illumination angle ranging from 30° to 100°. By use of the SLO unit of the second ophthalmic imaging apparatus 120, an annular fundus image of a donut-shaped region encircling a circular region centered on the visual axis CL may be obtained. By use of the OCT unit, OCT-3D volume data of an annular region may be obtained, and 3D data analyses and various maps may be created. Retinal tomography images in the annular region may also be obtained by use of the OCT unit.

Figure 18:
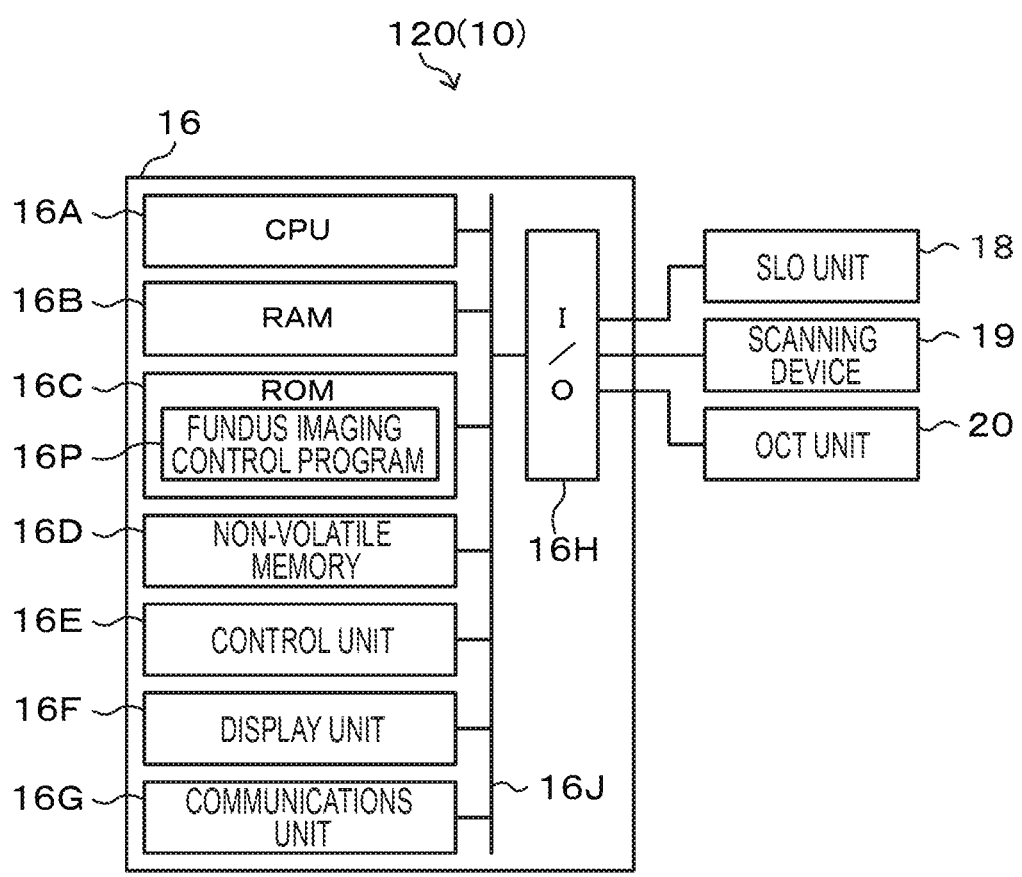
FIG. 18 is a block diagram showing an example of structure of an ophthalmic imaging apparatus according to the third exemplary embodiment.

FIG. 18 schematically shows an example of the control device 16 constituted by a computer in the ophthalmic imaging apparatus 10 according to either of the first exemplary embodiment and second exemplary embodiment, including the practical examples, which functions as the second ophthalmic imaging apparatus 120.

The control device 16 is constituted by a computer in which a CPU 16A, RAM 16B, ROM 16C and input/output interface (I/O) 16H are connected via a bus 16J to be capable of exchanging commands and data. A non-volatile memory 16D, a control unit 16E, a display unit 16F and a communications unit 16G are connected to the I/O interface 16H. Initial data of various kinds is memorized in advance in the non-volatile memory 16D. The communications unit 16G performs data communications with external equipment or the network 130. In the present exemplary embodiment, the communications unit 16G performs image data communications with the image server 140 or the image display terminal 150 via the network 130. The apparatus main body 14, the scanning device 19 and the OCT unit 20 are also connected to the I/O interface 16H.

The display unit 16F includes a device that displays images and various kinds of information. The control unit 16E includes entry equipment such as a keyboard and mouse or the like at which data and commands to be utilized in the control device 16 are entered. The control unit 16E and the display unit 16F may be combined together in hardware by a display unit such as a touch panel, which displays soft keys that accept control instructions and displays various kinds of information, or the like.

The ROM 16C stores a fundus imaging control program 16P that causes the control device 16 to execute fundus imaging control. The fundus imaging control program 16P includes a processing function that images the surroundings of the fundus central portion around the visual axis CL and obtains a surrounding image. That is, the CPU 16A reads the fundus imaging control program 16P from the ROM 16C, loads the fundus imaging control program 16P into the RAM 16B, and executes fundus imaging control processing in accordance with the fundus imaging control program 16P. When the CPU 16A executes the fundus imaging control processing, the ophthalmic imaging apparatus 10 is operated as the first ophthalmic imaging apparatus 110 by the control device 16. The fundus imaging control program 16P may be supplied on a recording medium such as a CD-ROM or the like.

The first ophthalmic imaging apparatus 110 is similar in structure to the second ophthalmic imaging apparatus 120 apart from functions that image the fundus central portion around the visual axis CL and obtain images. Accordingly, detailed descriptions of the first ophthalmic imaging apparatus 110 are not given here. Where the first ophthalmic imaging apparatus 110 and the second ophthalmic imaging apparatus 120 are distinguished in the descriptions, the control device of the first ophthalmic imaging apparatus 110 is labeled as a control device 15. To simplify the descriptions of the present exemplary embodiment below, an image of the fundus central portion around the visual axis CL that is captured by the first ophthalmic imaging apparatus 110 is memorized at the image server 140 in association with a patient ID, which is acquired in advance, representing a patient of whose subject eye 12 the image is acquired.

Although not shown in the drawings, the image server 140 includes a storage device that stores captured images in association with patient IDs. The image server 140 features functions that store captured images and that output captured images retrieved using patient IDs as an identifier. Patient-related information is also stored at the image server 140 in association with the patient ID, such as the patient's name, hospital visit dates and so forth. That is, the image server 140 is a server that is configured to be connectable to the first ophthalmic imaging apparatus 110, the second ophthalmic imaging apparatus 120 and the image display terminal 150 and that features functions for conducting exchanges of data between the equipment. The image server 140 also features functions for recording patient data—such as images captured by the first ophthalmic imaging apparatus 110 and second ophthalmic imaging apparatus 120, imaging conditions, patient IDs, names and so forth—and information relating to examinations and examination results.

The image display terminal 150 is a terminal at which an image viewer is installed. The image viewer is software for displaying, on the basis of information from the image server 140, patient information and images of patients such as fundus images, retinal images and the like. The image viewer features electronic health record functions. Electronic health record functions include a function for doctors to enter examination results, a function for booking hospital visits, and a function for outputting imaging instructions to a clinical technician at the ophthalmic imaging apparatus.

Figure 19:
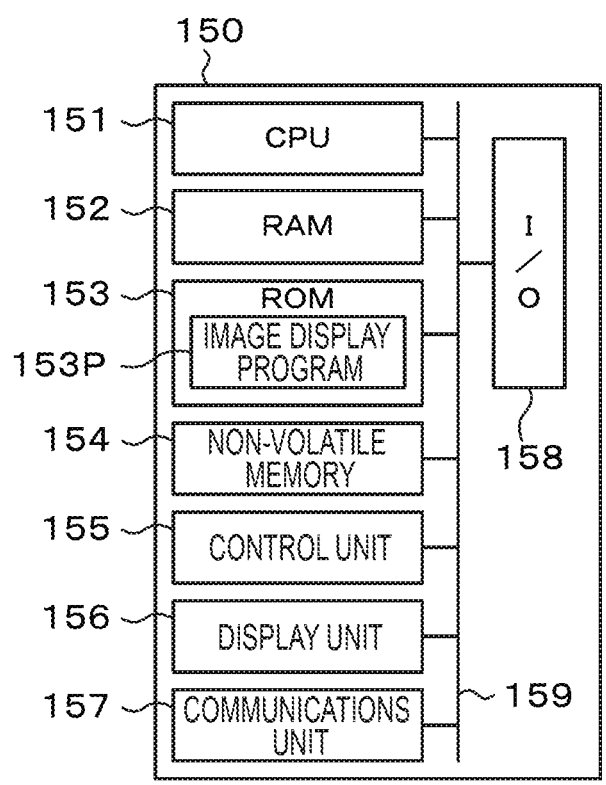
FIG. 19 is a block diagram showing an example of structure of an image display terminal according to the third exemplary embodiment.

FIG. 19 schematically shows an example of the image display terminal 150 constituted by a computer.

The image display terminal 150 is constituted by a computer in which a CPU 151, RAM 152, ROM 153 and input/output interface (I/O) 158 are connected via a bus 159 to be capable of exchanging commands and data. A non-volatile memory 154, a control unit 155, a display unit 156 and a communications unit 157 are connected to the I/O interface 158. Initial data of various kinds is memorized in advance in the non-volatile memory 154. The communications unit 157 performs data communications with external equipment or the network 130. In the present exemplary embodiment, the communications unit 157 performs image data communications with the image server 140 or the image display terminal 150 via the network 130.

The display unit 156 includes a device that displays images and various kinds of information. The control unit 155 includes entry equipment such as a keyboard 155K and mouse 155M or the like at which data and commands to be utilized in the control device 16 are entered. The control unit 155 and the display unit 156 may be combined together in hardware by a display unit such as a touch panel or the like, which displays soft keys that accept control instructions and displays various kinds of information, or the like.

The ROM 153 stores an image display program 153P that causes the image display terminal 150 to execute fundus image display control. The image display program 153P includes a processing function that synthesizes a captured image of the first fundus image region 12G1 at the fundus central portion with a captured image of the second fundus image region 12G2 surrounding the fundus central portion and displays the two-dimensional image 12G (details of the function are described below). The CPU 151 reads the image display program 153P from the ROM 153, loads the image display program 153P into the RAM 152, and executes image display control processing in accordance with the image display program 153P. When the CPU 151 executes the image display control processing, the image display terminal 150 operates as a device that displays the two-dimensional image 12G of the whole of the imageable region 12A. The image display program 153P may be supplied on a recording medium such as a CD-ROM or the like.

In the present exemplary embodiment, a situation is described in which the image display terminal 150 that displays fundus images is structured separately from the first ophthalmic imaging apparatus 110 and the second ophthalmic imaging apparatus 120. However, structures are possible in which the image display terminal 150 is combined with one or both of the first ophthalmic imaging apparatus 110 and the second ophthalmic imaging apparatus 120.

Now, operation of the present exemplary embodiment is described.

Figure 20:
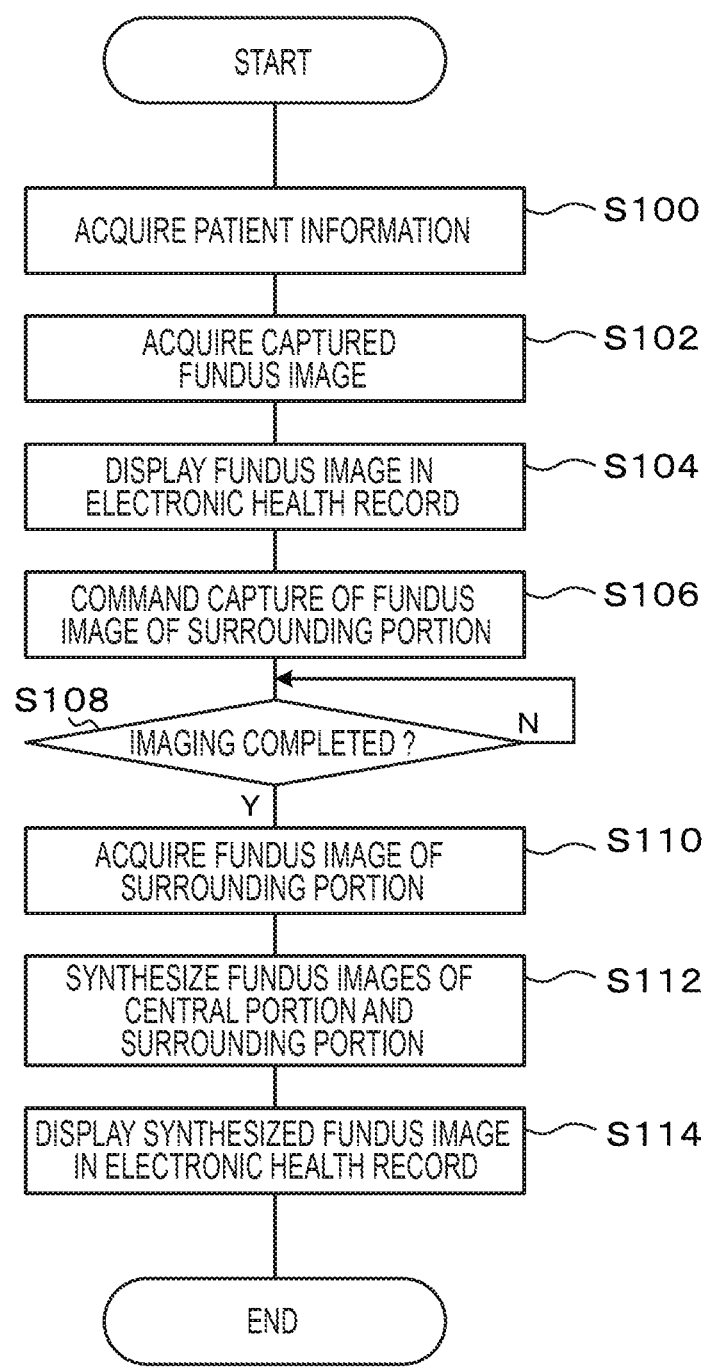
FIG. 20 is a flowchart showing an example of a flow of processing that is executed by the image display terminal according to the third exemplary embodiment.

FIG. 20 shows a flow of processing of the image display program 153P that is executed at the image display terminal 150. The image display program 153P is executed by the CPU 151, for example, when a power supply to the image display terminal 150 is turned on.

Figure 21:
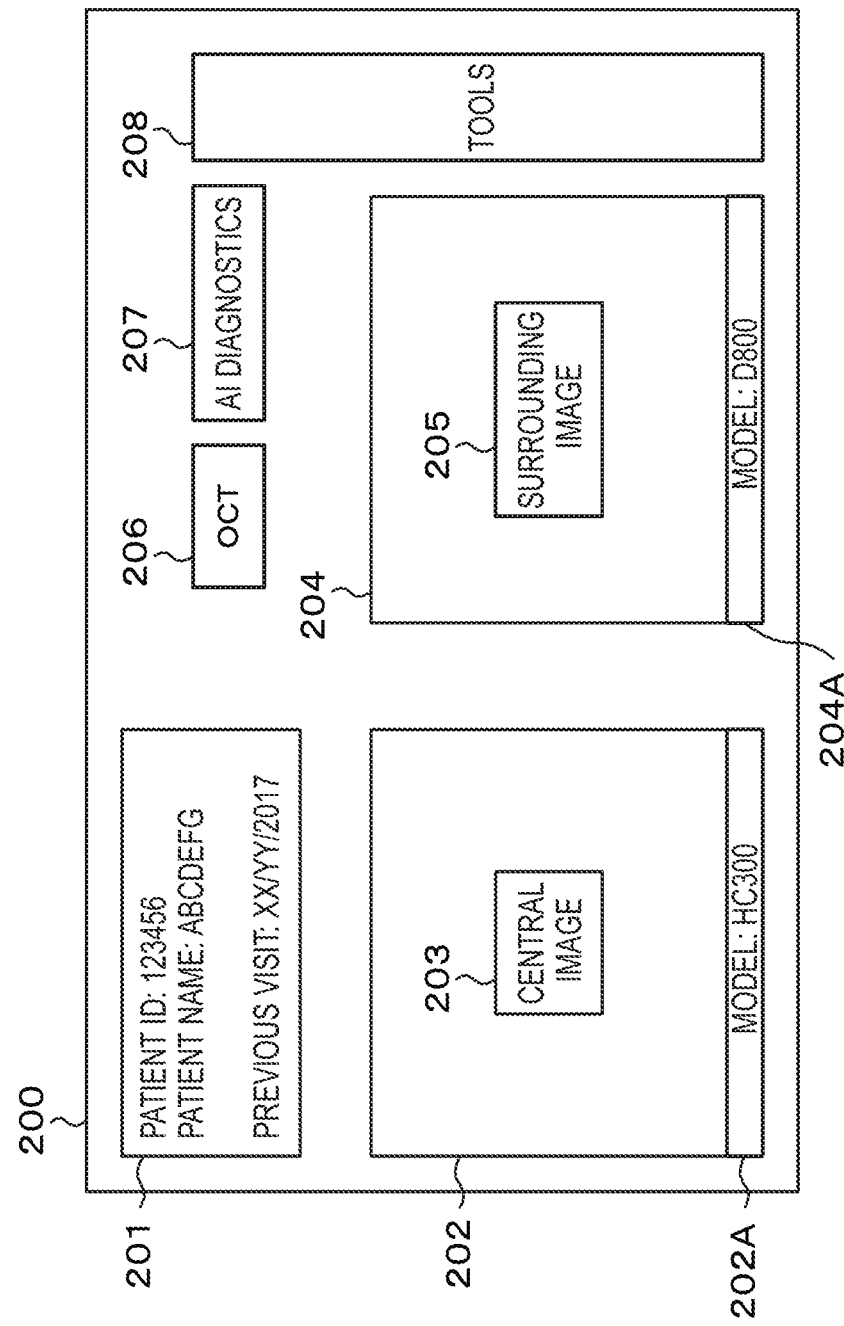
FIG. 21 is a conceptual image showing an example of a display screen at a display unit according to the third exemplary embodiment.

FIG. 21 shows an electronic health record screen 200, which is an example of a display screen displayed at the display unit 156 when the power supply to the image display terminal 150 has been turned on.

The electronic health record screen 200 is provided with a display region 201 that displays information relating to the patient with the subject eye 12, a display region 202 that displays a captured image of the first fundus image region 12G1 of the fundus central portion, and a display region 204 that displays a captured image of the second fundus image region 12G2 surrounding the fundus central portion. A display region 202A that displays information identifying the model of the first ophthalmic imaging apparatus 110 imaging the first fundus image region 12G1 is adjacent to the display region 202. A command button 203 for acquiring a captured image with the first ophthalmic imaging apparatus 110 is provided inside the display region 202. A display region 204A that displays information identifying the model of the second ophthalmic imaging apparatus 120 imaging the second fundus image region 12G2 is adjacent to the interior of the display region 204. A command button 205 for acquiring a captured image with the second ophthalmic imaging apparatus 120 is provided inside the display region 204. A command button 206 for imaging the fundus with the OCT function, a command button 207 for commanding the execution of diagnostics of the images with artificial intelligence, and a command button 208 for instructing various settings of the screen 200 are also included in the electronic health record screen 200.

In step S100 shown in FIG. 20, patient information acquisition processing is executed, and the acquired patient information is displayed at the display unit 156. More specifically, when the control unit 155 accepts entry of a patient ID by a user, the CPU 151 requests patient information associated with the patient ID from the image server 140, acquires corresponding information from the image server 140, and displays the patient information in the display region 201. As an example of the patient information, FIG. 21 shows a situation in which the patient ID representing the patient with the subject eye 12, a patient name, and information representing the date of a previous hospital visit by the patient are acquired and displayed.

Then, in step S102, a fundus image of the patient that has been captured is acquired and, in step S104, is displayed in the electronic health record. More specifically, when the control unit 155 detects a press input of the command button 203 for acquiring a captured image with the first ophthalmic imaging apparatus 110, the CPU 151 requests a captured image from the first ophthalmic imaging apparatus 110, which is associated with the patient ID at the image server 140, acquires the captured image from the image server 140 in response, and displays the captured image in the display region 202.

Figure 22:
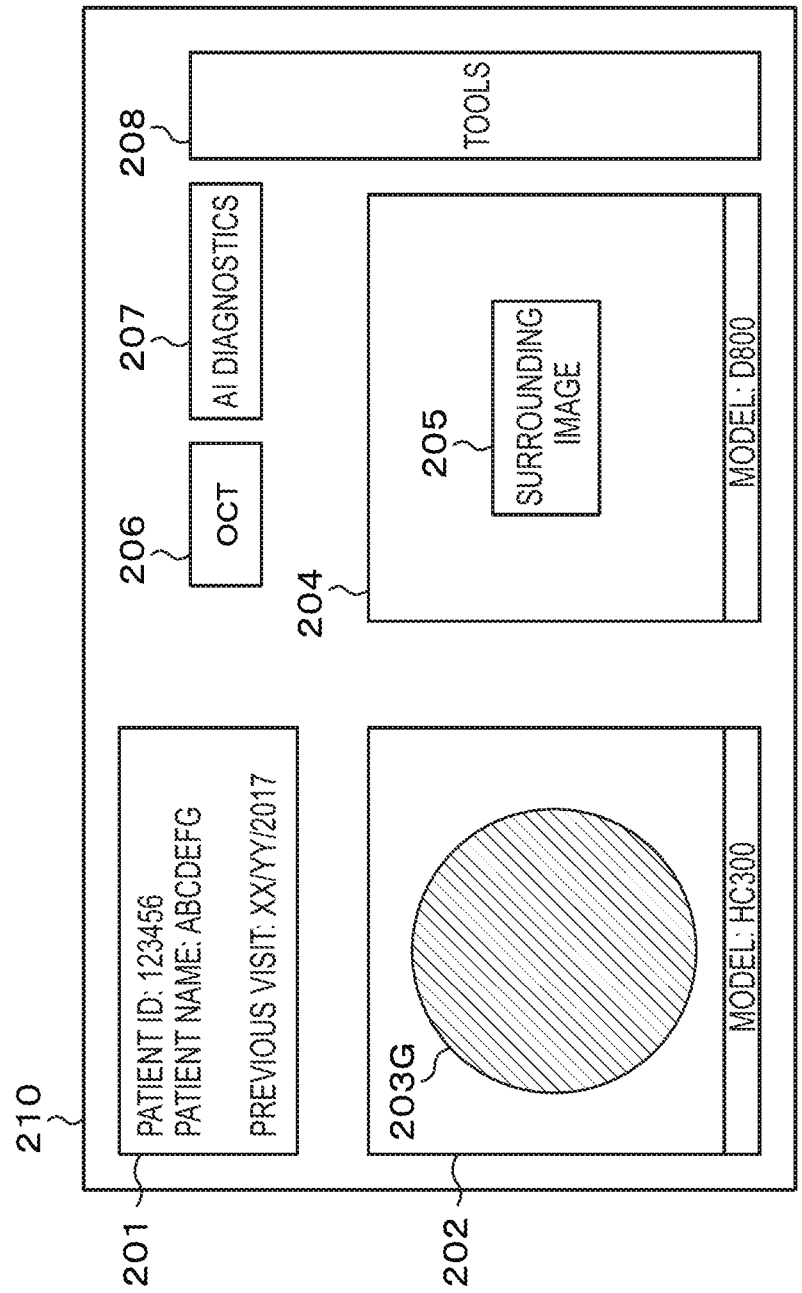
FIG. 22 is a conceptual image showing an example of a display screen at the display unit according to the third exemplary embodiment.

FIG. 22 shows an example of an electronic health record screen 210 in which a captured image 203G from the first ophthalmic imaging apparatus 110 is displayed in the display region 202.

In step S106 in FIG. 20, image command processing for image capture of the second fundus image region 12G2 surrounding the fundus central portion is executed. Until this imaging is completed, the result of the determination in step S108 is negative. When the result of the determination in step S108 is affirmative, in step S110, a captured image in which the fundus surrounding the central portion of the subject eye 12 according to the patient ID is acquired. That is, when the control unit 155 detects a press input of the command button 205 for acquiring a captured image with the second ophthalmic imaging apparatus 120, the CPU 151 outputs a command to image the fundus surrounding the central portion of the subject eye 12 according to the patient ID to the second ophthalmic imaging apparatus 120. The second ophthalmic imaging apparatus 120 receives the command from the image display terminal 150, images the fundus surrounding the central portion of the subject eye 12 according to the patient ID, and outputs the captured image to the image display terminal 150. Processing may be executed to output the fundus image of the surroundings of the central portion of the subject eye 12 and the captured image via the image server 140.

In step S112, image processing is executed to synthesize the image captured by the first ophthalmic imaging apparatus 110 that is acquired in step S102 with the image captured by the second ophthalmic imaging apparatus 120 that is acquired in step S110. In step S114, the image synthesized by this image processing is displayed at the display region 204 as the two-dimensional image 12G of the whole of the imageable region 12A.

The synthesis processing of the captured image 203G from the first ophthalmic imaging apparatus 110 with a captured image 205G from the second ophthalmic imaging apparatus 120 may be, for example, processing that uses 3D data or scan data obtained from the OCT units 20 to create a three-dimensional image, sectional images and a surface image, and that executes segmentation processing. The fundus image may also be created by using data obtained from the respective SLO units 14.

When synthesizing the images, it is sufficient to execute, for example, image processing such as rotation, magnification/reduction and the like of the images such that patterns of blood vessels in the images are superposed. The synthesized image may provide a wide-angle image as if a wide-angle image of 100° were captured by ophthalmic equipment for capturing wide-angle images. It will be clear that the image processing that synthesizes the images is not limited to the techniques mentioned above and that widely known techniques may be employed. The synthesized image is memorized and stored at the image server 140.

Figure 23:
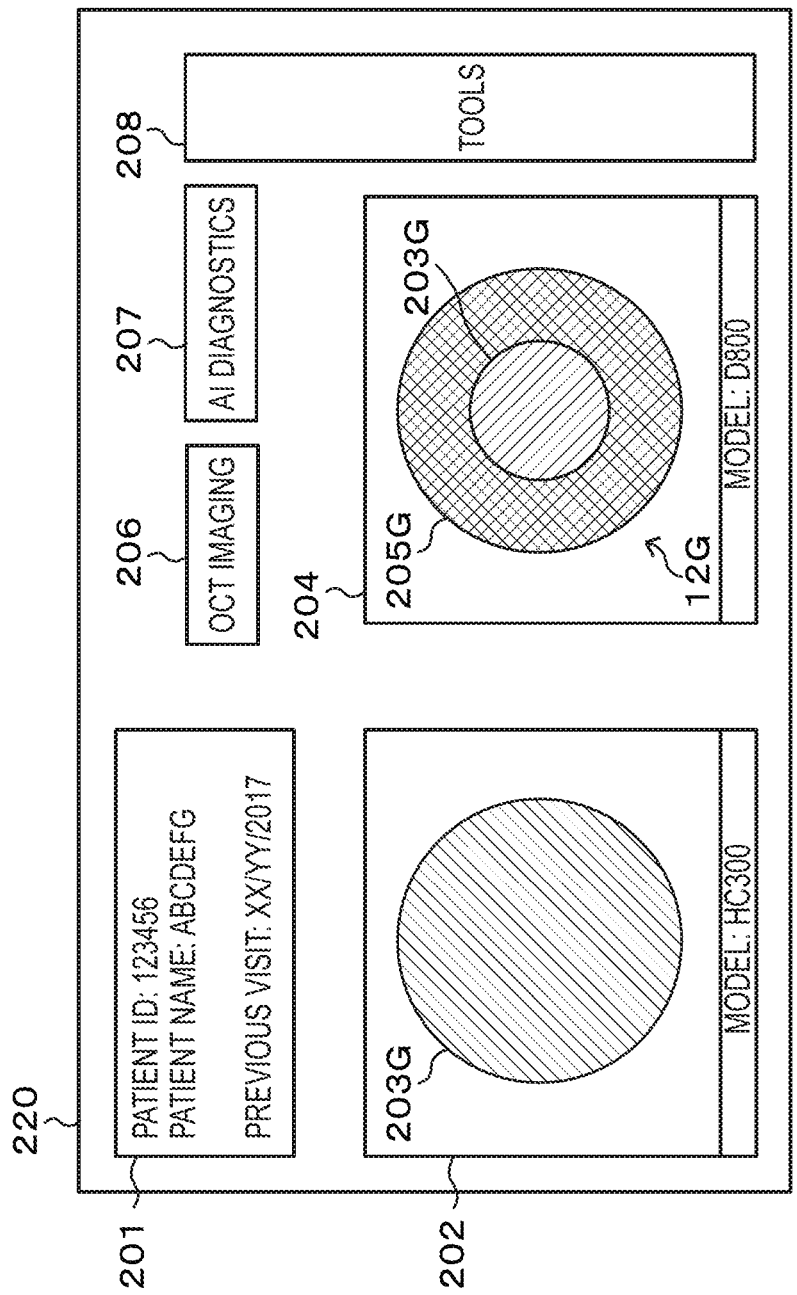
FIG. 23 is a conceptual image showing an example of a display screen at the display unit according to the third exemplary embodiment.

FIG. 23 shows an example of an electronic health record screen 220 in which the two-dimensional image 12G synthesized from the captured image 203G from the first ophthalmic imaging apparatus 110 and the captured image 205G from the second ophthalmic imaging apparatus 120 is displayed in the display region 204.

As described above, in the third exemplary embodiment, an image of the fundus center and an image of the surroundings of the fundus central portion are synthesized to obtain the two-dimensional image 12G of the whole of the imageable region 12A. Thus, a wide-angle image may be obtained as if a wide-angle image of, for example, 100° were captured by ophthalmic equipment for capturing wide-angle images.

The imaging system 100 according to the third exemplary embodiment functions excellently when an ophthalmologist is observing and examining the fundus of the subject eye 12. That is, in the imaging system 100 according to the third exemplary embodiment, an examination is performed on the basis of the synthesized fundus image, and examination results are entered using the electronic health record functions of the image viewer. When AI diagnostics are to be applied to a fundus image C, a button V14 is pressed/clicked in an interface, which is not shown in the drawings, to switch to an AI diagnostics mode. When examination of OCT images is required, a button V13 is pressed/clicked to switch to an OCT mode.

An ophthalmologist both may use a high-resolution fundus image of the central portion with an imaging angle of 30° to accurately examine the fundus central portion, such as the optic disc and the macula, and may use the fundus image C synthesized to correspond to an imaging angle of 100° to accurately identify the presence or absence of lesions in retina periphery portions.

Many ophthalmologists keep ophthalmic equipment in order to use high-resolution images of the fundus and retina for examinations. High-resolution ophthalmic equipment has imaging angles in the range of 10° to 30°; it is difficult to image peripheral portions of the fundus and retina beyond this range. Consequently, it is necessary for an ophthalmologist to separately purchase wide-angle or ultrawide-angle ophthalmic equipment for the periphery portions of the fundus and retina. In contrast, when the imaging system 100 according to the third exemplary embodiment is employed, ophthalmic equipment that is present may be employed efficiently without the purchase of new wide-angle or ultra-wide-angle ophthalmic equipment. High-resolution images of the central portion of the fundus and retina may be used for examinations, and periphery portions of the fundus and retina may be examined in synthesized fundus images with wide angles exceeding 100°.

In the practical examples described above, descriptions are given with an imaging angle α of an ophthalmic apparatus 1 being 30° and an imaging angle β of a surroundings imaging ophthalmic apparatus 2 being 30°-100°, but this is not limiting. The imaging angle of the surroundings imaging ophthalmic apparatus 2 may be set as appropriate for the imaging angle of the ophthalmic apparatus 1. For example, the imaging angle of the surroundings imaging ophthalmic apparatus 2 may be set in combinations such as an imaging angle of the ophthalmic apparatus of 45° with an imaging angle of the surroundings imaging ophthalmic apparatus 2 of 45°-100°, or an imaging angle of the ophthalmic apparatus of 55° with an imaging angle of the surroundings imaging ophthalmic apparatus 2 of 55°-120°.

A maximum imaging angle of the surroundings imaging ophthalmic apparatus 2 is set to 120°, but the optical system may be adjusted to set the maximum imaging angle above 120°. Various imaging angle settings may be modified so as to satisfy the requirements of ophthalmologists.

In consideration of image processing procedures, settings may be made such that an outer periphery portion of the circular imaging region according to the ophthalmic apparatus 1 is superposed with an inner periphery portion of the annular imaging region according to the surroundings imaging ophthalmic apparatus 2, in combinations such as an imaging angle of the ophthalmic apparatus of 30° with an imaging angle of the periphery imaging ophthalmic apparatus 2 of 25°-80°, an imaging angle of the ophthalmic apparatus of 45° with an imaging angle of the periphery imaging ophthalmic apparatus 2 of 40°-100°, or an imaging angle of the ophthalmic apparatus of 55° with an imaging angle of the periphery imaging ophthalmic apparatus 2 of 45°-120°.

In the exemplary embodiments described above, polygon mirrors and mirror galvanometers are mentioned as examples of the first optical scanner 22, the second optical scanner 24 and the third optical scanner 29, but this is not limiting. For example, alternative optical elements that are capable of scanning scanned light in the Y direction may be employed. For example, micro-electromechanical systems (MEMS) mirrors, rotating mirrors, prisms and oscillating mirrors can be mentioned.

Obviously, the scanning devices described for the above exemplary embodiments may perform similar scanning with the X direction and the Y direction exchanged.

In an optical system that is capable of imaging surrounding regions with an ultrawide angle, stray light may be prevented by providing a shading screen in a central region containing the optical axis. Stray light may be reduced by limiting the illumination regions of scanned light from the SLO unit 18 and the OCT unit 20 to annular regions of the imaging field of view.

The present invention has been described using exemplary embodiments, but the technical scope of the present invention is not to be limited to the scope described in the above exemplary embodiments. Numerous modifications and improvements may be applied to the above exemplary embodiments within a scope not departing from the gist of the invention, and modes to which these modifications and/or improvements are applied are to be encompassed by the technical scope of the invention. All references, patent applications and technical specifications cited in the present specification are incorporated by reference into the present specification to the same extent as if the individual references, patent applications and technical specifications were specifically and individually recited as being incorporated by reference.

EXPLANATION OF THE REFERENCE SYMBOLS

10 Ophthalmic imaging apparatus
12 Subject eye
12A Imageable region
12A1 First imageable region
12A2 Second imageable region
16 Control device
19 Scanning device
28 Common optical system
28A Optical system
A External illumination angle

The invention claimed is:

1. An ophthalmic imaging optical system comprising a first optical unit and a second optical unit that are disposed on the same optical axis in this order from a side thereof at which a subject eye is disposed, wherein:
the first optical unit includes:
a first reflection surface that includes an aperture portion centered on the optical axis; and
a second reflection surface that reflects light reflected from the first reflection surface toward an opposite side of the subject eye, and
the first optical unit and the second optical unit form a conjugate position that is conjugate with a pupil position of the subject eye, at an opposite side of the subject eye,
the first reflection surface and the second reflection surface are formed with rotational symmetry about the optical axis,
the first optical unit is disposed such that light from the pupil of the subject eye is transmitted through a refracting surface which is concave relative to the subject eye and is disposed closest to the subject eye, and reflected by the first reflection surface and the second reflection surface, and passed through the aperture portion of the first reflection surface,
the first reflection surface is a reflective surface that is formed in a concave shape,
the second reflection surface is a reflective surface that is formed in a convex shape and includes an aperture centered on the optical axis,
the first and second reflection surfaces form an annular image of a portion of the subject eye,
the first reflection surface is a reflective surface formed at a surface of a material with a refractive index greater than 1, and reflects light that is incident through the material with the refractive index greater than 1, and
the second reflection surface includes an aperture portion that transmits light at a central portion thereof containing the optical axis.

2. The ophthalmic imaging optical system according to claim 1, wherein:
the first reflection surface and the second reflection surface are formed at each of two opposing sides of a material with a refractive index greater than 1, and are reflecting surfaces that reflect light that is incident through the material with the refractive index greater than 1,
the second reflection surface includes an aperture portion centered on the optical axis, and
the aperture portion of the first reflection surface and the aperture portion of the second reflection surface are transmitting apertures that respectively transmit light.

3. The ophthalmic imaging optical system according to claim 1, wherein:
the first reflection surface and the second reflection surface are reflectors with gas at the incidence sides thereof, and
the second optical unit includes a first lens with a positive refractive power and a second lens with a negative refractive power.

4. The ophthalmic imaging optical system according to claim 1, wherein the first optical unit and the second optical unit are respectively disposed on an optical axis of the ophthalmic imaging optical system.

5. An ophthalmic imaging apparatus comprising:
the ophthalmic imaging optical system according to claim 1;
a scanning component that is disposed at the pupil conjugate position and scans light from a light source toward the subject eye.

6. The ophthalmic imaging apparatus according to claim 5, wherein the ophthalmic imaging optical system is configured to enable incident light from the pupil of the subject eye to enter into the refracting surface that is disposed at the side closest to the subject eye and is concave relative to the subject eye with at least a 100° angle of an external illumination angle, and the ophthalmic imaging optical system enables fundus imaging with an angle of at least 100°.

7. An ophthalmic imaging optical system comprising a first optical unit and a second optical unit that are disposed on the same optical axis in this order from a side thereof at which a subject eye is disposed, wherein:
the first optical unit includes:
a first reflection surface that includes an aperture portion centered on the optical axis; and
a second reflection surface that reflects light reflected from the first reflection surface toward an opposite side of the subject eye, and
the first optical unit and the second optical unit form a conjugate position that is conjugate with a pupil position of the subject eye, at an opposite side of the subject eye,
the first reflection surface and the second reflection surface are formed with rotational symmetry about the optical axis, the first optical unit is disposed such that light from the pupil of the subject eye is transmitted through a refracting surface which is concave relative to the subject eye and is disposed closest to the subject eye, and reflected by the first reflection surface and the second reflection surface, and passed through the aperture portion of the first reflection surface, the first reflection surface is a reflective surface that is formed in a concave shape, the second reflection surface is a reflective surface that is formed in a convex shape and includes an aperture centered on the optical axis, the first and second reflection surfaces form an annular image of a portion of the subject eye, and the first optical unit and the second optical unit are formed so as to satisfy the conditional expression:

$$0.1 < D \cdot \tan(A/2)/S < 1.0$$

wherein D represents a distance from a vertex of the refracting surface that is disposed at the side closest to the subject eye with the concave surface facing the side at which the subject eye is disposed to a center of the pupil of the subject eye, S represents a maximum effective diameter of the refracting surface in the first optical unit, and A represents an external illumination angle from the pupil.

8. The ophthalmic imaging optical system according to claim 7, wherein:

the ophthalmic imaging optical system having the first optical unit and the second optical unit includes a lens group with a positive refractive power disposed between a fundus conjugate position that is conjugate with a fundus of the subject eye and a pupil conjugate position that is conjugate with the pupil of the subject eye, and the lens group includes at least one surface with a negative refractive power.

9. The ophthalmic imaging optical system according to claim 7, wherein the first optical unit and the second optical unit are structured in accordance with the conditional expression:

$$1 < |\beta| < 10$$

where $\beta$ represents an imaging magnification between the pupil position of the subject eye and a position of a pupil conjugate that is conjugate with the pupil position.

10. An optometric image acquisition method for synthesizing an annular image with a circular image and acquiring a wide-angle fundus image, the optometric image acquisition method comprising:

a first step of acquiring the circular image;
a second step of acquiring the annular image; and
a third step of synthesizing the circular image with the annular image and acquiring a wide-angle fundus image.

11. An optometric image acquisition method according to claim 10, wherein the circular image is imaged by a first fundus apparatus with an imaging angle of $\alpha$, and the annular image is imaged by a second fundus apparatus with an imaging angle from $\alpha$ to $\beta$, a being less than $\beta$.

12. An optometric imaging system comprising:

a first acquisition section that acquires an annular first image of a subject eye portion imaged by an ophthalmic imaging apparatus;

a second acquisition section that acquires a circular second image of a portion of the subject eye corresponding to an opening of an annular aperture portion; and a third acquisition section that synthesizes the annular first image acquired by the first acquisition section with the second image acquired by the second acquisition section and acquires a third image that is a synthesized wide-angle image.

13. The optometric imaging system according to claim 12, wherein the ophthalmic imaging apparatus comprises a first optical unit and a second optical unit that are disposed on the same optical axis in this order from a side thereof at which a subject eye is disposed, wherein:

the first optical unit includes:
a first reflection surface that includes an aperture portion centered on the optical axis; and
a second reflection surface that reflects light reflected from the first reflection surface toward an opposite side of the subject eye, and the first optical unit and the second optical unit form a conjugate position that is conjugate with a pupil position of the subject eye, at an opposite side of the subject eye.

14. The optometric imaging system according to claim 13, wherein the first reflection surface and the second reflection surface are formed with rotational symmetry about the optical axis.

15. The optometric imaging system according to claim 14, wherein:

the first optical unit is disposed such that light from the pupil of the subject eye is transmitted through a refracting surface which is concave relative to the subject eye and is disposed closest to the subject eye, and reflected by the first reflection surface and the second reflection surface, and passed through the aperture portion of the first reflection surface.

16. The optometric imaging system according to claim 15, wherein:

the first reflection surface is a reflective surface that is formed in a concave shape, the second reflection surface is a reflective surface that is formed in a convex shape and includes an aperture centered on the optical axis, and the first and second reflection surfaces form an annular image of a portion of the subject eye.

* * * * *